US008383876B2

(12) United States Patent
Robles et al.

(10) Patent No.: US 8,383,876 B2
(45) Date of Patent: Feb. 26, 2013

(54) ABSORBENT ARTICLES WITH PATTERNS OF INDICATING

(75) Inventors: Miguel Alvaro Robles, Wyoming, OH (US); Mattias Schmidt, Idstein (DE); Donald Carroll Roe, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 387 days.

(21) Appl. No.: 12/646,393

(22) Filed: Dec. 23, 2009

(65) Prior Publication Data

US 2010/0168699 A1 Jul. 1, 2010

Related U.S. Application Data

(63) Continuation-in-part of application No. 12/346,520, filed on Dec. 30, 2008, now abandoned.

(51) Int. Cl.
*A61F 13/15* (2006.01)
*A61F 13/20* (2006.01)
(52) U.S. Cl. ........................ 604/361; 604/358
(58) Field of Classification Search .................. 604/361, 604/358, 385.01
See application file for complete search history.

(56) References Cited

U.S. PATENT DOCUMENTS

| | | | |
|---|---|---|---|
| 5,078,708 A | 1/1992 | Haque | |
| 6,297,424 B1 | 10/2001 | Olson et al. | |
| 6,710,221 B1 | 3/2004 | Pierce et al. | |
| 2001/0008683 A1 | 7/2001 | Takai et al. | |
| 2002/0007162 A1 | 1/2002 | Cammarota et al. | |
| 2003/0078553 A1 | 4/2003 | Wada et al. | |
| 2003/0130631 A1 | 7/2003 | Springer et al. | |
| 2004/0138633 A1 | 7/2004 | Mishima et al. | |
| 2004/0254549 A1 | 12/2004 | Olson et al. | |
| 2005/0065489 A1 | 3/2005 | Driskell et al. | |
| 2006/0069362 A1 | 3/2006 | Odorzynski et al. | |
| 2006/0149197 A1 | 7/2006 | Niemeyer et al. | |
| 2006/0149204 A1 | 7/2006 | Niemeyer et al. | |
| 2006/0229578 A1* | 10/2006 | Roe et al. ...................... | 604/361 |
| 2008/0086060 A1 | 4/2008 | Kritzman et al. | |
| 2008/0147031 A1 | 6/2008 | Long et al. | |
| 2008/0208151 A1 | 8/2008 | Zacharias et al. | |
| 2008/0228157 A1 | 9/2008 | McKiernan et al. | |
| 2008/0294134 A1* | 11/2008 | Schroer, Jr. ................... | 604/361 |
| 2009/0326494 A1* | 12/2009 | Uchida et al. ................. | 604/361 |
| 2010/0168695 A1 | 7/2010 | Robles et al. | |
| 2010/0168696 A1 | 7/2010 | Robles et al. | |
| 2010/0168697 A1 | 7/2010 | Robles et al. | |
| 2010/0168698 A1 | 7/2010 | Robles et al. | |
| 2010/0168699 A1 | 7/2010 | Robles et al. | |
| 2010/0168700 A1 | 7/2010 | Schmidt et al. | |
| 2010/0168701 A1 | 7/2010 | Schmidt et al. | |

FOREIGN PATENT DOCUMENTS

| | | |
|---|---|---|
| DE | 85 06 388 U1 | 6/1985 |
| DE | 20 2006 00816 | 3/2007 |
| EP | 0 705 089 B1 | 5/1997 |
| EP | 0705089 B1 | 5/1997 |

(Continued)

OTHER PUBLICATIONS

U.S. Appl. No. 12/646,296, filed Dec. 23, 2009, Robles, et al.

(Continued)

*Primary Examiner* — Susan Su
(74) *Attorney, Agent, or Firm* — Betty J. Zea; Charles R. Ware

(57) ABSTRACT

An absorbent article comprises a number of visual fullness indicating areas arranged in a distinct pattern. The pattern has an overall shape that is triangular or trapezoidal.

11 Claims, 10 Drawing Sheets

FOREIGN PATENT DOCUMENTS

| | | |
|---|---|---|
| EP | 0 925 769 A2 | 6/1999 |
| FR | 2 695 824 B1 | 3/1994 |
| JP | 2001-095845 | 4/2001 |
| KR | 98039173 | 8/1998 |
| WO | WO 95/00099 A1 | 1/1995 |
| WO | WO 99/16401 | 4/1999 |
| WO | WO 01/95845 A1 | 12/2001 |
| WO | WO 2005/030084 A2 | 4/2005 |
| WO | WO 2005/102238 A1 | 11/2005 |

OTHER PUBLICATIONS

U.S. Appl. No. 12/646,315, filed Dec. 23, 2009, Robles, et al.
U.S. Appl. No. 12/646,334, filed Dec. 23, 2009, Robles, et al.
U.S. Appl. No. 12/646,354, filed Dec. 23, 2009, Robles, et al.
U.S. Appl. No. 12/646,414, filed Dec. 23, 2009, Schmidt, et al.
U.S. Appl. No. 12/646,430, filed Dec. 23, 2009, Schmidt, et al.
Lambi Premium Diapers manufactured by Lambi, Mexico as advertised for sale on the Bella Baby Boutique website on Apr. 30, 2009 shown in size Large.
International Search Report, PCT/US2009/069569, mailed May 19, 2010, 17 pages.
International Search Report, PCT/US2009/069559, mailed Feb. 17, 2010, 12 pages.
International Search Report, PCT/US2009/069579, mailed Apr. 22, 2010, 12 pages.
International Search Report, PCT/US2009/069570, mailed Apr. 22, 2010, 12 pages.
International Search Report, PCT/US2009/069572, mailed May 7, 2010, 16 pages.
International Search Report, PCT/US2009/069659, mailed Jun. 7, 2010, 17 pages.
International Search Report, PCT/US2009/069656, mailed Jun. 7, 2010, 17 pages.
All Office Actions, U.S. Appl. No. 12/646,296.
All Office Actions, U.S. Appl. No. 12/646,315.
All Office Actions, U.S. Appl. No. 12/646,334.
All Office Actions, U.S. Appl. No. 12/646,354.
All Office Actions, U.S. Appl. No. 12/646,414.
All Office Actions, U.S. Appl. No. 12/646,430.

* cited by examiner

ABSORBENT ARTICLES WITH PATTERNS OF INDICATING

CROSS REFERENCE TO RELATED APPLICATIONS

This application is a continuation-in-part of U.S. application Ser. No. 12/346,520, filed Dec. 30, 2008 now abandoned, the substance of which is hereby incorporated by reference.

FIELD

In general, embodiments of the present disclosure relate to wetness indicating for absorbent articles. In particular, embodiments of the present disclosure relate to visual fullness indicating for absorbent articles.

BACKGROUND

Absorbent articles can absorb liquid bodily exudates such as sweat, blood, urine, menses, etc. An absorbent article can include a wetness indicator. The wetness indicator can indicate the presence of a liquid bodily exudate in the article. Unfortunately, some wetness indicators for absorbent articles can be difficult to understand. If the signal from a wetness indicator is misunderstood then the absorbent article may be changed too soon. The wearer may underutilize the capacity of the article. If the signal from a wetness indicator is misunderstood then the absorbent article may be changed too late. The bodily exudates may exceed the capacity of the article resulting in leaks.

SUMMARY

Figure 1A:
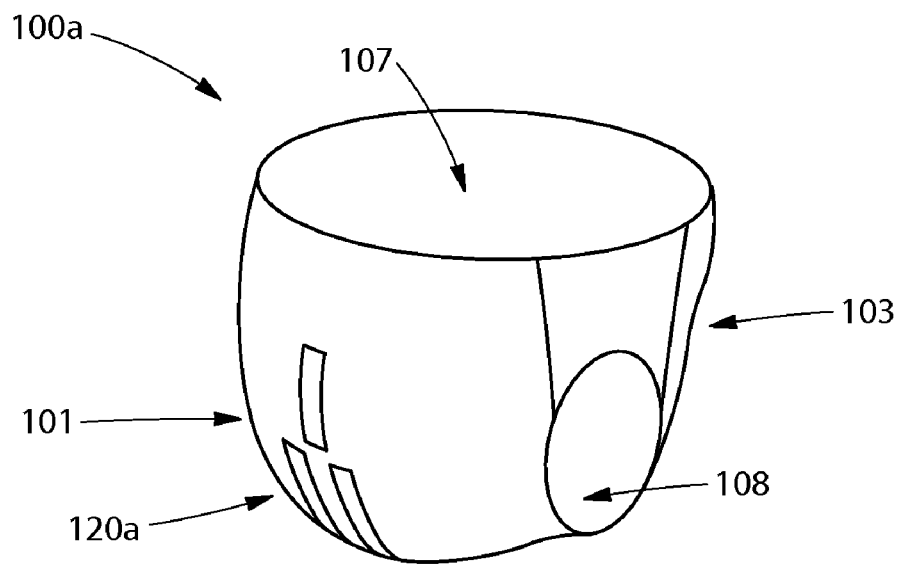
FIG. 1A illustrates a pant-type disposable wearable absorbent article with a pattern of visual fullness indicating areas in the front, according to embodiments of the present disclosure.

The present disclosure includes absorbent articles with wetness indicating areas that are easy to understand. The wetness indicating areas are easy to understand because they are arranged in particular patterns.

As an example, an absorbent article can have wetness indicating areas arranged in a pattern having an overall shape with varying widths. The overall shape can be triangular or trapezoidal. The visual fullness indicating areas can change visual states in sequence; first the inboard areas then the outboard areas.

The width of the pattern can indicate how full an absorbent article is. For instance, a change in visual state in a wider inboard portion can indicate that the absorbent article is somewhat filled while a change in visual state in a narrower outboard portion can indicate that the absorbent article is approaching full. The visual state changes in these different widths can provide differing visual signals. These differing visual signals can be easily understood as indicating differing degrees of fullness.

The absorbent articles of the present disclosure are also easy to understand because they have wetness indicating areas arranged in indicating zones. The zones can have differing numbers of indicating areas. As an example, a first indicating zone can have a first number of indicating areas and a second indicating zone can have a second number of indicating areas. The indicating areas can change visual states in sequence; first the areas of the first zone then the indicating areas of the second indicating zone.

The number of changed indicating areas can indicate how full an absorbent article is. For instance, a change in visual state in a first number of indicating areas can indicate that the absorbent article is somewhat filled while a change in visual state in a second number of indicating areas can indicate that the absorbent article is approaching full. The visual state changes in these different numbers of indicating areas can provide differing visual signals. These differing visual signals can be easily understood as indicating differing degrees of fullness.

An absorbent article having indicating areas arranged in such patterns and/or zones can help provide certainty about the fullness of the absorbent article. By knowing how full an article is, the article can be changed after the wearer has appropriately utilized the capacity of the article. Also, by knowing how full an article is, the article can be changed before it is likely to leak.

DETAILED DESCRIPTION

The indicating patterns of the present disclosure can be used with all kinds of absorbent articles. An absorbent article can absorb liquid bodily exudates such as sweat, blood, urine, menses, etc. An absorbent article can be a product or a material. Examples of absorbent articles include products and/or materials for sanitary protection, hygienic use, and/or wound care.

Some absorbent articles are disposable. A disposable absorbent article is configured to be partly or wholly disposed of after a single use. A disposable absorbent article is configured such that the soiled article, or a soiled portion of the article, is not intended to be restored and reused (e.g., not intended to be laundered). Examples of disposable absorbent articles include wound care products, such as bandages and dressings, as well as feminine care products, such as pads and liners. Disposable absorbent articles can use embodiments of the present disclosure.

Some absorbent articles are wearable. A wearable absorbent article is configured to be worn on or around a body of a wearer. Wearable absorbent articles can also be disposable. Examples of disposable wearable absorbent articles include disposable diapers and disposable incontinence undergarments. A disposable wearable absorbent article can receive and contain bodily exudates while being worn by a wearer. In some embodiments, a disposable wearable absorbent article can include a topsheet, an absorbent core, an outer cover, a waist opening, and leg openings. Disposable wearable absorbent articles can use embodiments of the present disclosure.

One kind of wetness indicator for an absorbent article is a visual fullness indicator. A wetness indicator is considered visual if it can indicate the presence of a liquid bodily exudate by its visual state. Throughout the present disclosure, unless otherwise stated, the presence of a liquid bodily exudate refers to the presence of a concentration of the liquid bodily exudate that is sufficient to cause a visual wetness indicator to change visual states. A wetness indicator is considered a fullness indicator if it can indicate the degree to which a liquid bodily exudate has filled an absorbent article. A visual fullness indicator can indicate the presence of a liquid bodily exudate by a wet edge that moves along the indicator such that the indicator progressively changes visual states. A visual fullness indicator can include one or more visual fullness indicating areas. An indicating area is a defined continuous two-dimensional region, configured to indicate the presence of a liquid bodily exudate by its visual state. As examples, in various embodiments, an indicator can comprise a series of indicating areas or a pattern of indicating areas.

The figures of the present disclosure are intended to illustrate elements, their parts, and their relationships, as described in the specification; the figures are not intended to illustrate any particular relative or absolute size or dimension, unless otherwise stated in the text.

FIGS. 1A-2C illustrate various disposable wearable absorbent articles, each with one or more patterns of indicating areas. For clarity, FIGS. 1A-2C do not illustrate all details of the visual fullness indicating areas or of the disposable wearable absorbent articles. Each pattern of visual fullness indicating areas in FIGS. 1A-2C can be any embodiment of a pattern of visual fullness indicating areas of the present disclosure.

FIG. 1A illustrates an outside perspective view of a front 101 and a side 103 of a pant-type disposable wearable absorbent article 100A formed for wearing. The pant-type disposable wearable absorbent article 100A includes a waist opening 107 and a leg opening 108. The absorbent article 100A includes a pattern 120A of visual fullness indicating areas disposed in the front 101.

Throughout the present disclosure, a reference to a pant-type disposable wearable absorbent article can refer to an embodiment that is side-fastenable or to an embodiment without fasteners. A reference to a pant-type disposable wearable absorbent article can also refer to an article with preformed waist and/or leg openings or to an embodiment that is not preformed. Thus, each embodiment of an absorbent article of the present disclosure that is described as pant-type can be configured in any of these ways, as will be understood by one of ordinary skill in the art.

Figure 1B:
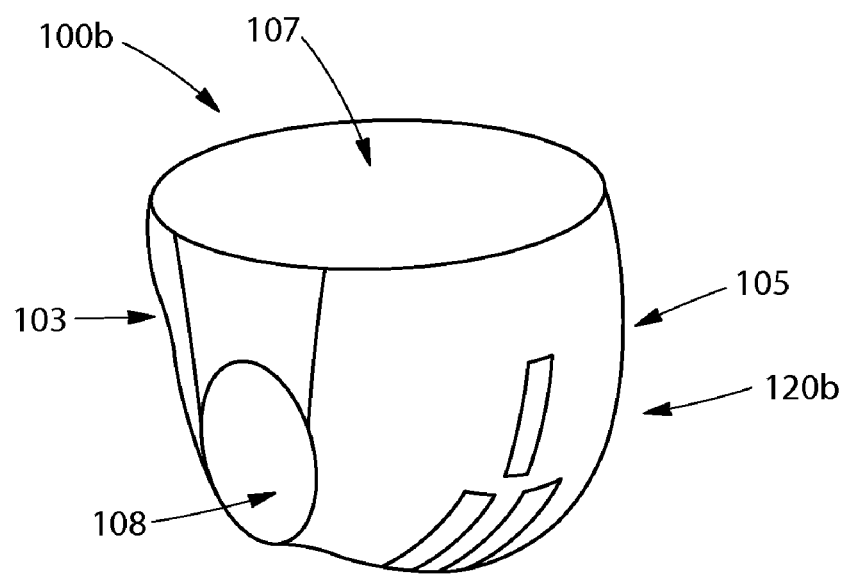
FIG. 1B illustrates a pant-type disposable wearable absorbent article with a pattern of visual fullness indicating areas in the back, according to embodiments of the present disclosure.

FIG. 1B illustrates an outside perspective view of a side 103 and a back 105 of a pant-type disposable wearable absorbent article 100B formed for wearing. The pant-type disposable wearable absorbent article 100B includes a waist opening 107 and a leg opening 108. The absorbent article 100B includes a pattern 120B of visual fullness indicating areas in the back 105.

Figure 1C:
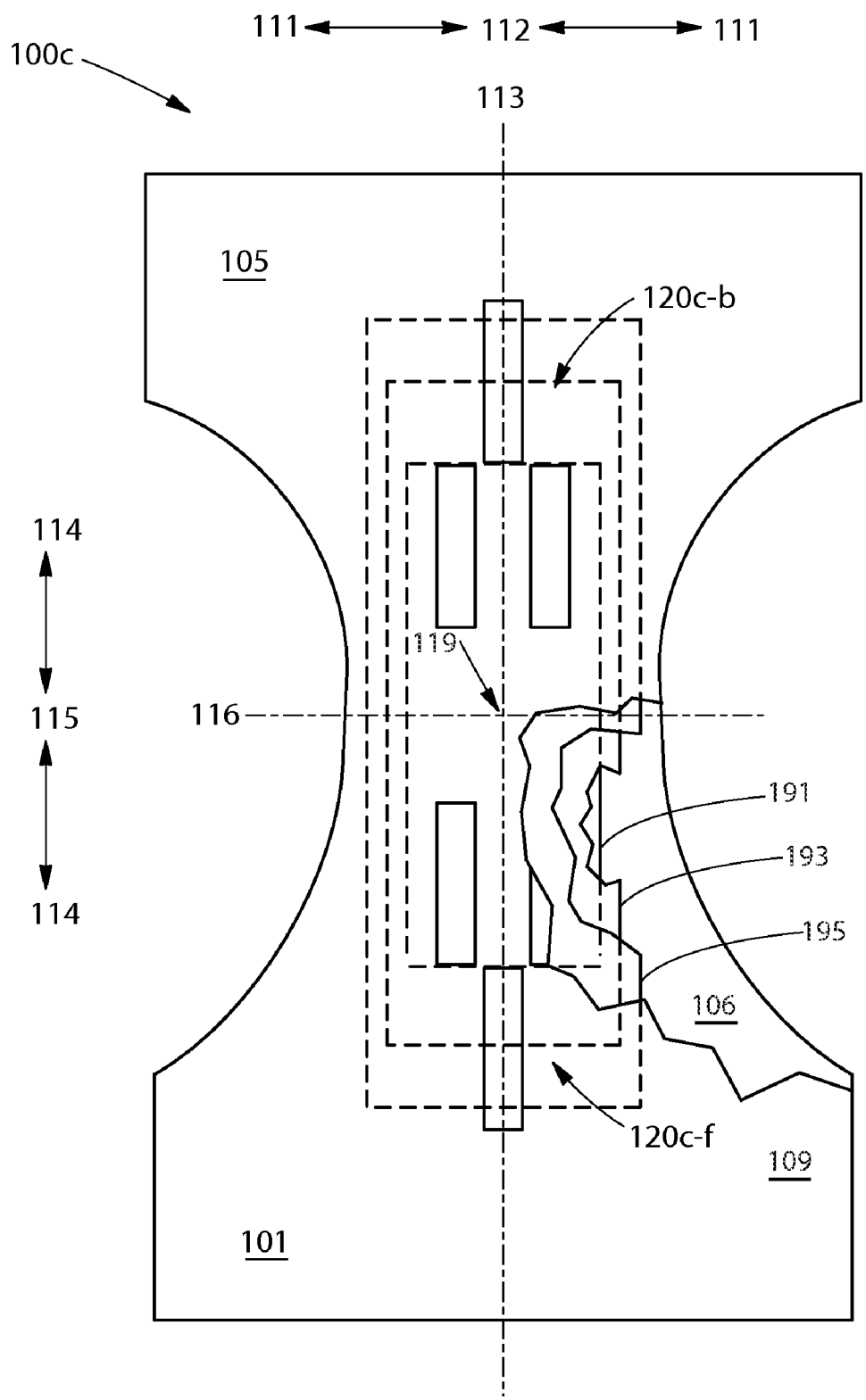
FIG. 1C illustrates a pant-type disposable wearable absorbent article with a number of patterns of visual fullness indicating areas, according to embodiments of the present disclosure.

FIG. 1C illustrates an outside plan view of a pant-type disposable wearable absorbent article 100C laid out flat. The disposable wearable absorbent article 100C includes a front 101 and a back 105, which are separated by a lateral centerline 116.

In FIG. 1C, a longitudinal centerline 113 and the lateral centerline 116 provide lines of reference for referring to relative locations of the disposable wearable absorbent article 100C. When a first location is nearer to the longitudinal centerline 113 than a second location, the first location can be considered laterally inboard 112 to the second location. Similarly, the second location can be considered laterally outboard 111 from the first location. When a third location is nearer to the lateral centerline 116 than a fourth location, the third location can be considered longitudinally inboard 115 to the fourth location. Also, the fourth location can be considered longitudinally outboard 114 from the third location.

A reference to an inboard location, without a lateral or longitudinal limitation, refers to a location of the disposable wearable absorbent article 100C that is laterally inboard and/or longitudinally inboard to another location. In the same way, a reference to an outboard location, without a lateral or longitudinal limitation, refers to a location of the disposable wearable absorbent article 100C that is laterally outboard and/or longitudinally outboard from another location.

Inboard and outboard can also be understood with reference to a center of a disposable wearable absorbent article. The longitudinal centerline 113 and the lateral centerline 116 cross at a center 119 of the disposable wearable absorbent article 100C. When one location is nearer to the center 119 than another location, the one location can be considered inboard to the other location. The one location can be inboard laterally, or longitudinally, or both laterally and longitudinally. The other location can be considered outboard from the one location. The other location can be outboard laterally, or longitudinally, or both laterally and longitudinally.

FIG. 1C includes arrows indicating relative directions for laterally outboard 111, laterally inboard 112, longitudinally outboard 114, and longitudinally inboard 115, each with respect to the disposable wearable absorbent article 100C.

Throughout the present disclosure, a reference to a longitudinal dimension, measurement, line, or direction refers to a dimension, measurement, line, or direction that is substantially or completely parallel to the longitudinal centerline 113 and a reference to a lateral dimension, measurement, line, or direction refers to a dimension, measurement, line, or direction that is substantially or completely parallel to the lateral centerline 116. The terminology for describing relative locations, as discussed above, is used for disposable wearable absorbent articles throughout the present disclosure. This terminology can also be similarly applied to various other absorbent articles, as will be understood by one of ordinary skill in the art.

The disposable wearable absorbent article 100C includes a topsheet 106, an outer cover 109, an acquisition layer 191, a distribution layer 193, and an absorbent core 195. A portion of the outer cover 109 is shown as broken to illustrate a portion of the topsheet 106 and a portion of the absorbent core 195. A portion of the absorbent core 195 is shown as broken to illustrate a portion of the distribution layer 193. A portion of the distribution layer 193 is shown as broken to illustrate a portion of the acquisition layer 191.

The disposable wearable absorbent article 100C includes patterns of visual fullness indicating areas in exemplary locations and orientations. The disposable wearable absorbent article 100C includes a front pattern 120C-F of visual fullness indicating areas along the longitudinal centerline 113 in the front 101. The disposable wearable absorbent article 100C also includes a back pattern 120C-B of visual fullness indicating areas along the longitudinal centerline 113 in the back 105.

In the disposable wearable absorbent article 100C, the patterns of visual fullness indicating areas are oriented substantially radially out from the center 119. However, in addition to the locations and orientations illustrated in FIG. 1C, a pattern of visual fullness indicating areas of the present disclosure can be disposed in various alternate locations and orientations in an absorbent article, as will be understood by one of ordinary skill in the art. As an example, a visual fullness indicating area can be disposed in a pant-type disposable wearable absorbent article at a location relative to a pee point for a wearer of the article.

Figure 2A:
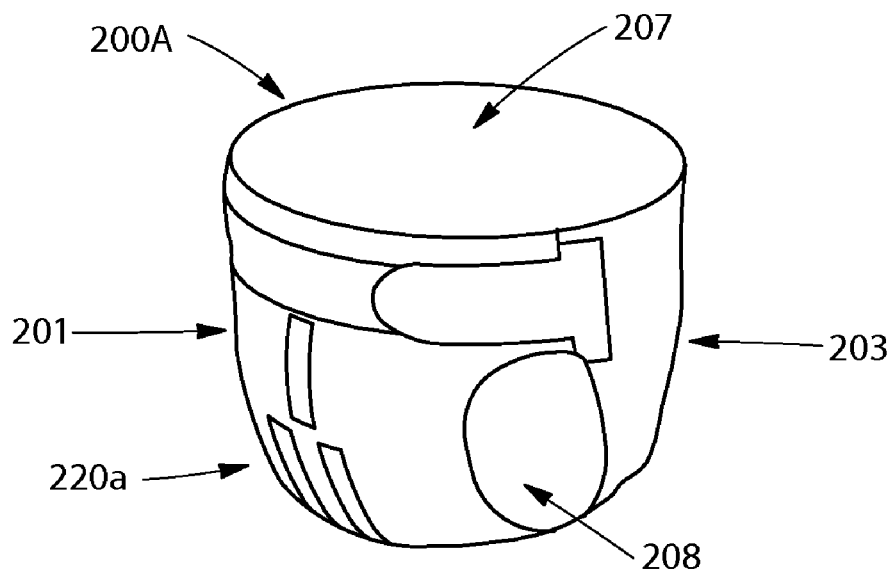
FIG. 2A illustrates a front-fastenable disposable wearable absorbent article with a pattern of visual fullness indicating areas in the front, according to embodiments of the present disclosure.

FIG. 2A illustrates an outside perspective view of a front 201 and a side 203 of a front-fastenable disposable wearable absorbent article 200A formed for wearing. The front-fastenable disposable wearable absorbent article 200A includes a waist opening 207 and a leg opening 208. The absorbent article 200A includes a pattern 220A of visual fullness indicating areas disposed in the front 201.

While the present disclosure refers to front-fastenable absorbent articles, the present disclosure also contemplates alternate embodiments of absorbent articles having patterns of indicating, as described herein, wherein the absorbent articles are rear-fastenable. Thus, each embodiment of an absorbent article of the present disclosure that is described as front-fastenable can also be configured to be rear fastenable, as will be understood by one of ordinary skill in the art.

Figure 2B:
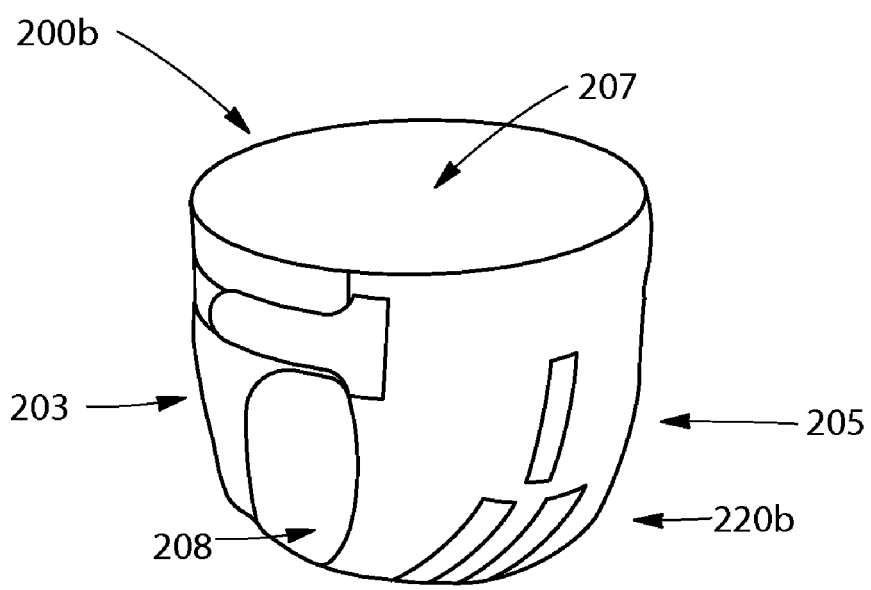
FIG. 2B illustrates a front-fastenable disposable wearable absorbent article with a pattern of visual fullness indicating areas in the back, according to embodiments of the present disclosure.

FIG. 2B illustrates an outside perspective view of a side 203 and a back 205 of a front-fastenable disposable wearable absorbent article 200B formed for wearing. The front-fastenable disposable wearable absorbent article 200B includes a waist opening 207 and a leg opening 208. The absorbent article 200B includes a pattern 220B of visual fullness indicating areas in the back 205.

Figure 2C:
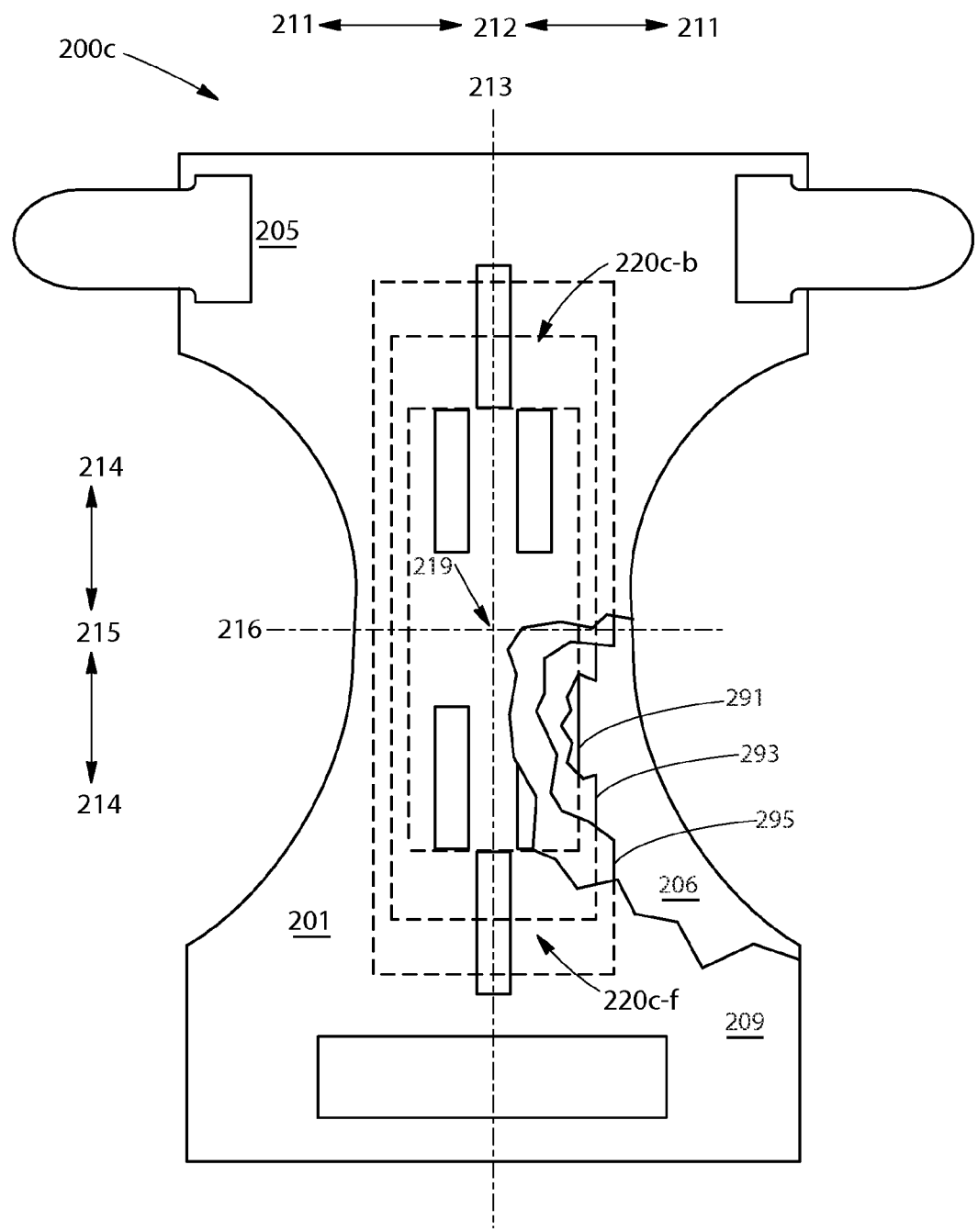
FIG. 2C illustrates a front-fastenable disposable wearable absorbent article with a number of patterns of visual fullness indicating areas, according to embodiments of the present disclosure.

FIG. 2C illustrates an outside plan view of a front-fastenable disposable wearable absorbent article 200C laid out flat. The disposable wearable absorbent article 200C includes a front 201, a back 205, a longitudinal centerline 213, and a lateral centerline 216.

The disposable wearable absorbent article 200C includes a topsheet 206, an outer cover 209, an acquisition layer 291, a distribution layer 293, and an absorbent core 295. A portion of the outer cover 209 is shown as broken to illustrate a portion of the topsheet 206 and a portion of the absorbent core 295. A portion of the absorbent core 295 is shown as broken to illustrate a portion of the distribution layer 293. A portion of the distribution layer 293 is shown as broken to illustrate a portion of the acquisition layer 291.

The disposable wearable absorbent article 200C includes patterns of visual fullness indicating areas in various exemplary locations and orientations. The disposable wearable absorbent article 200C includes a front pattern 220C-F of visual fullness indicating areas along the longitudinal centerline 213 in the front 201. The disposable wearable absorbent article 200C also includes a back pattern 220C-B of visual fullness indicating areas along the longitudinal centerline 213 in the back 205.

In the disposable wearable absorbent article 200C, the patterns of visual fullness indicating areas are oriented substantially radially out from the center 219. However, in addition to the locations and orientations illustrated in FIG. 2C, a pattern of visual fullness indicating areas of the present disclosure can be disposed in various alternate locations and orientations in an absorbent article, as will be understood by one of ordinary skill in the art. As an example, a pattern of visual fullness indicating areas can be disposed in a front-fastenable disposable wearable absorbent article at a location relative to a pee point for a wearer of the article.

Figure 3A:
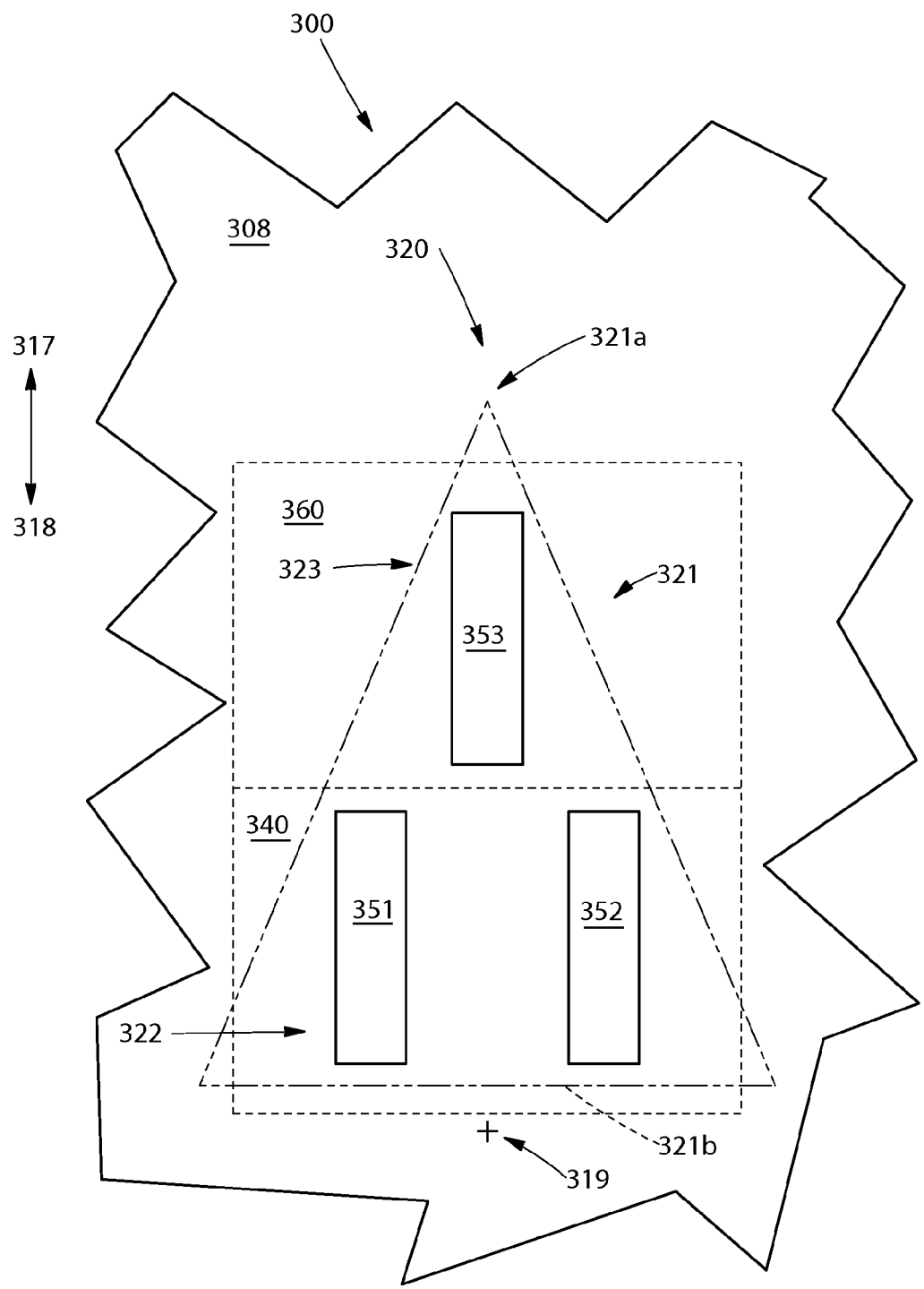
FIG. 3A illustrates a portion of an absorbent article with a pattern of visual fullness indicating areas arranged in two indicating zones wherein the pattern has an overall shape that is triangular, according to embodiments of the present disclosure.

FIG. 3A illustrates an outside plan view of a portion 308 of an absorbent article 300 laid out flat. In various embodiments, the absorbent article 300 can be a disposable wearable absorbent article, such as a pant-type disposable wearable absorbent article or a front-fastenable disposable wearable absorbent article. In FIG. 3A, outside edges of the portion 308 are broken lines, since the portion 308 is illustrated as separate from the rest of the absorbent article 300. For reference, FIG. 3A illustrates a center 319 of the absorbent article 300 and arrows indicating relative directions for outboard 317 and inboard 318 for the absorbent article 300.

The portion 308 of the absorbent article 300 includes a pattern 320 of visual fullness indicating areas. The pattern 320 is disposed offset from the center 319. In various embodiments, one or more parts of a visual fullness indicator can be disposed near, at, or overlapping a center of an absorbent article. For example, a single indicating area can extend from a front of an absorbent article, through the center of the absorbent article, to the back of the absorbent article. In such an embodiment, a farthest inboard point along the indicating area can be considered an inboard end of two indicators.

The pattern 320 of visual fullness indicating areas includes a first visual fullness indicating area 351, a second visual fullness indicating area 352, and a third visual fullness indicating area 353. In various embodiments, a pattern can include four or more visual fullness indicating areas. The pattern 320 has an inboard end 322 and an outboard end 323.

Each of the visual fullness indicating areas, 351, 352, and 353, has an overall shape that is substantially elongated. In various embodiments a visual fullness indicating area can have an overall shape that is more or less elongated. In some embodiments, part, or parts, or all of a visual fullness indicating area can be straight, curved, angled, segmented, or any regular or irregular geometric shape (such as a square, rectangle, triangle, trapezoid, octagon, hexagon, star, half circle, a quarter circle, a half oval, a quarter oval, a radial pattern, etc.), a recognizable image (such as a letter, number, word, character, face of an animal, face of a person, etc.), or another recognizable image (such as a plant, a car, etc.), another shape, or combinations of any of these shapes. In various embodiments, a visual fullness indicating area can have varying widths over part, or parts, or all of its length.

A visual fullness indicator is a visually distinct and recognizable pathway of one or more visual indicators and/or visual indicating areas. A pathway is recognizable in its visual context. In other words, a pathway is distinct and recognizable, when compared with the appearance of a surrounding area.

The pathway of a visual fullness indicator has two defined ends, a middle between the two ends, and a defined length from its one end to its other end. A visual fullness indicator can have one or more widths, each of which is less than its defined length.

A visual fullness indicator can be configured in various forms. For example, a visual fullness indicator can be formed by a single, continuous indicating area disposed along a pathway. As another example, a visual fullness indicator can be formed by a plurality of discrete indicators and/or discrete indicating areas disposed along a pathway.

Each of the visual fullness indicating areas, 351, 352, and 353, has an overall width that is substantially uniform. Each of the visual fullness indicating areas, 351, 352, and 353, has an overall shape that is substantially rectangular. In the embodiment of FIG. 3A, each of the visual fullness indicating areas 351, 352, and 353 has the same size and shape. In some embodiments, a pattern of visual fullness indicating areas can include visual fullness indicating areas wherein part, or parts, or all of some or all of the visual fullness indicating areas can differ in size and shape.

In embodiments of the present disclosure, visual fullness indicating areas can be arranged in a recognizable pattern having a distinct overall shape. In some embodiments, the visual fullness indicating areas of a pattern may be all of the wetness indicators included in an absorbent article. In other embodiments, where an absorbent article includes a pattern of visual fullness indicating areas as well as one or more other wetness indicators, some or all of the visual fullness indicating areas of the pattern can be spaced apart from some or all of the other wetness indicators, so the pattern can be more easily recognized. In some embodiments, where an absorbent article includes a pattern of visual fullness indicating areas as well as one or more other wetness indicating areas, it may be sufficient for only the visual fullness indicating areas at the outboard end of the pattern to be spaced apart from the other wetness indicators.

In embodiments of the present disclosure, the visual fullness indicating areas of a pattern can be spaced apart from other wetness indicators by various spaced apart distances. As an example, in embodiments where an absorbent article includes a pattern of visual fullness indicating areas as well as one or more other wetness indicators, some or all of the visual fullness indicating areas of the pattern can be spaced apart from some or all of the other wetness indicators by a spaced apart distance of at least 10 millimeters, at least 15 millimeters, at least 20 millimeters, at least 25 millimeters, or at least 30 millimeters. As another example, in embodiments where an absorbent article includes a pattern of visual fullness indicating areas as well as one or more other wetness indicators, some or all of the visual fullness indicating area(s) of an outboard end of the pattern can be spaced apart from some or all of the other wetness indicators by a spaced apart distance of at least 10 millimeters, at least 15 millimeters, at least 20 millimeters, at least 25 millimeters, or at least 30 millimeters.

In embodiments of the present disclosure, a pattern of visual fullness indicating areas can be recognized as having a distinctive overall shape. A distinctive overall shape can be recognized by one skilled in the art of visual pattern recognition, by identifying a number of visual fullness indicating areas that are disposed as a group in relatively close proximity to each other, and by observing that an outline of the group matches or approximates a distinctive shape. The present disclosure contemplates two distinctive shapes: the triangle and the trapezoid, each described in further detail below.

The visual fullness indicating areas 351, 352, and 353 are arranged in the pattern 320 such that the pattern 320 is recognizable as having a distinctive overall shape 321. In the embodiment of FIG. 3A, the overall shape 321 of the pattern 320 is triangular. However, in various embodiments, an overall shape of a pattern may only be substantially triangular. The triangular overall shape 321 includes a base 321B disposed proximate to the inboard end 322 as well as a vertex 321A disposed proximate to the outboard end 323. The triangular overall shape 321 is an isosceles triangle. However, in various embodiments, a pattern of visual fullness indicating areas can have a triangular overall shape that can be any kind of triangle, such as an equilateral triangle, a scalene triangle, a right triangle, or an oblique triangle.

In embodiments of the present disclosure, visual fullness indicating areas can also be arranged in two or more indicating zones. An indicating zone is a rectangular area disposed on a portion of an outer surface of an absorbent article, wherein the zone includes at least a portion of at least one visual fullness indicating area. An indicating zone has an overall length measured from its farthest point inboard to its farthest point outboard. An indicating zone has an overall width measured perpendicular to its overall length.

In embodiments having a first indicating zone and a second indicating zone, the second indicating zone has an overall width that is equal to an overall width of the first indicating zone. A second indicating zone has an overall length that can be less than, equal to, or greater than a first indicating zone. A second indicating zone is immediately adjacent to a first indicating zone. Substantially all or all of a second indicating zone is outboard from a first indicating zone.

In the embodiment of FIG. 3A, the visual fullness indicating areas 351, 352, and 353, are arranged in a first indicating zone 340 and/or a second indicating zone 360. The first indicating zone 340 is a rectangular area within the portion 308 of the absorbent article 300, illustrated in FIG. 3A with dashed lines. The first indicating zone 340 has a first zone overall length and a first zone overall width. The second indicating zone 360 is another rectangular area with the portion 308 of the absorbent article 300, also illustrated in FIG. 3A with dashed lines. The second indicating zone 360 has a second indicating zone overall length and a second indicating zone overall width. In the embodiment of FIG. 3A, the second indicating zone overall width is equal to the first zone overall width and the second indicating zone overall length is equal to the first zone overall length. The second indicating zone 360 is immediately adjacent to the first indicating zone 340, and all of the second indicating zone 360 is outboard from the first indicating zone 340.

An indicating zone can include at least a portion of a number of visual fullness indicating areas. If any portion of a visual fullness indicating area lies within the area of the indicating zone then the indicating zone is considered to include a portion of the visual fullness indicating area. However, if an outer edge of a visual fullness indicating area merely coincides within a boundary of an indicating zone then the indicating zone would not be considered to include a portion of the visual fullness indicating area.

Throughout the present disclosure, the number of visual fullness indicating areas having at least a portion included in an indicating zone is expressed as a positive integer. As an example, if an indicating zone includes a small portion of a first visual fullness indicating area, a small portion of a second visual fullness indicating area, and a small portion of a third visual fullness indicating area, then the indicating zone would be considered as including at least a portion of three visual fullness indicating areas. As another example, if an indicating zone includes a small portion of a first visual fullness indicating area, a large portion of all of a second visual fullness indicating area, and all of a third visual fullness indicating area, then the indicating zone would also be considered as including at least a portion of three visual fullness indicating areas. As a further example, if an indicating zone includes all of a first visual fullness indicating area, all of a second visual fullness indicating area, and all of a third visual fullness indicating area, then the indicating zone would still be considered as including at least a portion of three visual fullness indicating areas.

In embodiments of the present disclosure, a first indicating zone can include at least a portion of each of a first number of visual fullness indicating areas and a second indicating zone can include at least a portion of each of a second number of visual fullness indicating areas, wherein the first number differs from the second number. In various embodiments, the second number can be greater than or less than the first number, as described below.

In the embodiment of FIG. 3A, the first indicating zone 340 includes all of the first visual fullness indicating area 351 and all of the second visual fullness indicating area 352. Thus, the first indicating zone 340 includes at least a portion of two visual fullness indicating areas; the first number is two. The second indicating zone 360 includes all of the third visual fullness indicating area 353. Thus, the second indicating zone 360 includes at least a portion of one visual fullness indicating area; the second number is one. In the embodiment of FIG. 3A, the first number (two) is greater than the second number (one).

Each of the visual fullness indicating areas, 351, 352, and 353, is in fluid communication with an absorbent core of the absorbent article 300 along its entire overall length. In various embodiments, a visual indicator can be configured such that part, or parts, or substantially all, or all of the indicator is in fluid communication with an absorbent core. In some embodiments, a visual indicator can be configured such that part, or parts, or substantially all, or all of the indicator overlaps an absorbent core or such that part, or parts, or substantially all, or all of the indicator does not overlap an absorbent core.

Throughout the present disclosure, fluid communication refers to a configured structural relationship that allows a liquid substance to freely pass from one element or location to another element or location; however, one element or location is not necessarily considered to be in fluid communication with another element or location merely by being connected or joined to a common element through which liquid can possibly pass. This definition of fluid communication is further explained by the following examples.

For example, if one element is configured to be in direct physical contact with another element such that a liquid substance can freely pass from the one element through the contacting portions to the other element, then the elements can be considered to be in fluid communication. As another example, if one element is connected to another element by a means for fluid communication such that a liquid substance can freely pass from the one element through the means for fluid communication to the other element, then the elements can be considered to be in fluid communication.

As a further example, if one element is connected to a substrate and another element is connected to the same substrate, but the substrate does not allow a liquid substance to freely pass through, then the elements are considered to be out of fluid communication. This holds true even if liquid can possibly pass through the substrate, so long as the liquid cannot pass through freely. The above definition of fluid communication, as explained through these examples, will be understood by one of ordinary skill in the art.

Throughout the present disclosure, the term liquid bodily exudate refers to any bodily substances exuded in liquid form (e.g. urine) and/or any liquid-like bodily substances (e.g. runny feces).

In various embodiments, part, or parts, or all of a visual fullness indicating area can be configured to change from one or more initial visual states to one or more subsequent visual states. Also, in embodiments of the present disclosure, for a particular portion of a visual fullness indicating area, an initial visual state and a subsequent visual can each be any visual state, so long as the subsequent visual state is visually distinguishable from the first initial visual state.

Throughout the present disclosure, the term visual state refers to an appearance which can be perceived by an unaided human with normal vision in standard lighting conditions. A visual state can comprise one or more colors, variations of color(s), patterns, letters, numbers, symbol, designs, images, and/or other visual devices. Colors include well known colors such as red, orange, yellow, green, blue, purple, etc. Variations of a color include variations in chroma, hue, and brightness, among others. While these informal terms are used for ease of reference, embodiments of the present disclosure are intended to encompass all colors which can be perceived by an unaided human with normal vision in standard lighting conditions.

In various embodiments, part, or parts, or all of a visual fullness indicating area can be configured to change from one or more initial visual states to one or more subsequent visual states. Also, in embodiments of the present disclosure, for a particular portion of a visual fullness indicating area, an initial visual state and a subsequent visual can each be any visual state, so long as the subsequent visual state is visually distinguishable from the first initial visual state.

Throughout the present disclosure, visual states are considered visually distinguishable if they can be recognized as different on sight by an unaided human with normal vision in standard lighting conditions. As an example, an unaided human with normal vision in standard lighting conditions should be able to recognize blue and yellow as different colors on sight. Thus, the blue and the yellow would be considered visually distinguishable visual states. As another example, an unaided human with normal vision in standard lighting conditions may be able to recognize a light shade of orange and a dark shade of orange as different shades of a color on sight. Thus, the light shade of orange and the dark shade of orange would be considered visually distinguishable visual states. As a further example, an unaided human with normal vision in standard lighting conditions may be able to recognize a first pattern and a second pattern as different visual states on sight. Thus, the first pattern and the second pattern would be considered visually distinguishable visual states.

As a still further example, an unaided human with normal vision in standard lighting conditions should be able to recognize an area with letters and a blank area as different visual states on sight. Thus, the area with letters and the blank area would be considered visually distinguishable visual states. Similarly, an area with numbers, symbols, designs, images, and/or other visual devices would also be considered visually distinguishable from a blank area or from a uniformly colored area. In addition to these examples, there are many other possible visually distinguishable visual states, as will be understood by one or ordinary skill in the art.

There are several ways by which absorbent articles of the present disclosure can be configured to include indicating areas that change visual states when indicating the presence of a bodily exudate, as will be understood by one of ordinary skill in the art. For example, an absorbent article can be configured to include such visual fullness indicators as described in the following U.S. Pat. No. 4,022,211, entitled "Wetness indicator for absorbent pads" issued on May 10, 1977 to Timmons, et al.; U.S. Pat. No. 4,231,370, entitled "Disposable diaper type garment having wetness indicator" issued on Nov. 4, 1980 to Mroz, et al.; U.S. Pat. No. 4,327,731, entitled "Moisture indicator" issued on May 4, 1982 to Powell; U.S. Pat. No. 4,681,576, entitled "Wetness indicating hot-melt adhesive" issued on Jul. 21, 1987 to Colon, et al.; U.S. Pat. No. 4,705,513, entitled "Disposable diaper with wetness indicator" issued on Nov. 10, 1987 to Sheldon, et al.; U.S. Pat. No. 4,738,674, entitled "Moisture indicator apparatus and method" issued on Apr. 19, 1988 to Todd, et al.; U.S. Pat. No. 4,743,238, entitled "Wetness indicating hot-melt adhesive" issued on May 10, 1988 to Colon et al.; U.S. Pat. No. 4,895,567, entitled "Wetness indicating hot-melt adhesive" issued on Jan. 23, 1990 to Colon et al.; U.S. Pat. No. 4,931,051, entitled "Wetness indicator" issued on Jun. 5, 1990 to Castello; U.S. Pat. No. 5,035,691, entitled "Hot melt moisture indicator material for disposable articles" issued on Jul. 30, 1991 to Zimmel, et al.; U.S. Pat. No. 5,066,711, entitled "Wetness indicating hot-melt adhesive" issued on Nov. 19, 1991 to Colon et al.; U.S. Pat. No. 5,089,548, entitled "Hot melt moisture indicator material for disposable articles" issued on Feb. 18, 1992 to Zimmel, et al.; U.S. Pat. No. 5,167,652, entitled "Moisture sensitive film" issued on Dec. 1, 1992 to Mueller; U.S. Pat. No. 5,342,861, entitled "Hot melt wetness indicator" issued on Aug. 30, 1994 to Raykovitz; U.S. Pat. No. 5,354,289 entitled "Absorbent product including super absorbent material and fluid absorption capacity monitor" issued on Oct. 11, 1994 to Mitchell, et al.; U.S. Pat. No. H1,376, entitled "Capacity indicia for absorbent articles" issued on Nov. 1, 1994 to Osborne, et al.; U.S. Pat. No. 5,647,863, entitled "Absorbent article with clean appearance and capacity signal means" issued on Jul. 15, 1997 to Hammons, et al.; U.S. Pat. No. 5,690,624, entitled "Disposable diaper" issued on Nov. 25, 1997 to Sasaki, et al.; U.S. Pat. No. 5,766,212, entitled "Disposable diaper" issued on Jun. 16, 1998 to Jitoe, et al.; U.S. Pat. No. 6,075,178, entitled "Absorbent article with wetness indicator" issued on Jun. 13, 2000; U.S. Pat. No. 6,515,194, entitled "Diaper having centrally-located chromatographic layer with peripherally-located wetness indicator" issued on Feb. 4, 2003 to Neading, et al.; U.S. Pat. No. 6,596,918, entitled "Absorbent articles having wetness indicating graphics and employing masking techniques" issued on Jul. 22, 2003 to Wehrle, et al.; U.S. Pat. No. 6,653,522, entitled "Hot melt adhesives based on sulfonated polyesters comprising wetness indicator" issued on Nov. 25, 2003 to Blumenthal, et al.; U.S. Pat. No. 6,772,708, entitled "Wetness indicator having improved colorant retention" issued on Aug. 10, 1994 to Klofta, et al.; U.S. Pat. No. 6,904,865, entitled "Wetness indicator having improved colorant retention and durability" issued on Jun. 14, 2005 to Klofta, et al.; U.S. Pat. No. 7,159,532, entitled "Wetness indicator having improved colorant retention and durability" issued on Jan. 9, 2007 to Klofta, et al.; U.S. Pat. No. 7,172,667, entitled "System and method for incorporating graphics into absorbent articles" issued on Feb. 6, 2007 to Vergona; U.S. Pat. No. 7,178,571, entitled "System and method for incorporating graphics into absorbent articles" issued on Feb. 20, 2007 to Vergona; U.S. Pat. No. 7,306,764, entitled "Wetness indicator" issued on Dec. 11, 2007 to Mody; and U.S. Pat. No. 7,332,642, entitled "Disposable absorbent articles having printed wetness indicators" issued on Feb. 19, 2008 to Liu, each of which is incorporated herein by reference.

In the embodiment of FIG. 3A, each of the visual fullness indicating areas 351, 352, and 353 is configured to change from one or more initial visual states to one or more subsequent visual states when indicating the presence of a liquid bodily exudate.

An absorbent article can be configured such that part, or parts, or all of a visual fullness indicating area is visible from outside of the absorbent article when the absorbent article is worn by a wearer. For example, a visual fullness indicating area can be visible when viewing an outside of an outer cover of an absorbent article. As a result, at least some of a subsequent visual state of the visual fullness indicating area will be visible from outside of the absorbent article.

The absorbent article 300 can be configured such that part, or parts, or all of each of the visual fullness indicating areas 351, 352, and 353 is visible from outside of the absorbent article 300 when the absorbent article 300 is worn by a wearer. As a result, at least some of the subsequent visual state(s) will be visible from outside of the absorbent article 300.

The pattern 320 can be configured such that the visual fullness indicating areas 351, 352, and 353 change visual states progressively and in sequence, as illustrated with FIGS. 3B-3E. First, the first visual fullness indicating area 351 and the second visual fullness indicating area 352 of the first indicating zone 340 can change from an initial visual state to a subsequent visual state when indicating the presence of a liquid bodily exudate to a first extent in an absorbent core of the absorbent article 300. Second, the third visual fullness indicating area 353 of the second indicating zone 360 can change from an initial visual state to a subsequent visual state when indicating the presence of a liquid bodily exudate to a second extent in an absorbent core of the absorbent article 300. The partial or complete absence or presence of the subsequent visual state(s) in the visual fullness indicating areas 351, 352, and 353 of the pattern 320 can indicate the fullness of the absorbent article 300.

Since the visual fullness indicating areas 351, 352, and 353 are arranged in a pattern with a distinct overall shape, the indicating areas are easy to understand. The wider inboard widths and the narrower outboard widths of the pattern 320 can help provide certainty about the fullness of the absorbent article 300. Also, since the visual fullness indicating areas 351, 352, and 353 are arranged in indicating zones, the indicating areas are easy to understand. The differing numbers of visual fullness indicating areas in the indicating zones can help provide certainty about the fullness of the article 300.

By knowing the fullness of the absorbent article 300, the absorbent article 300 can be changed after a wearer has appropriately utilized its capacity and/or before it is likely to leak. The benefits of patterns of visual indicating areas with differing widths and differing numbers are similarly provided in the embodiments of FIGS. 4, 5, 6, and 7, as described below.

FIGS. 3B-3E illustrate the pattern 320 of visual fullness indicating areas of the embodiment of FIG. 3A in various states of indication. The first visual fullness indicating area 351, the second visual fullness indicating area 352, and the third visual fullness indicating area 353 change visual states progressively and in sequence in the presence of a liquid bodily exudate to indicate the fullness of the absorbent article 300. In FIGS. 3B-3E, subsequent visual states are illustrated with hatching.

Figure 3B:
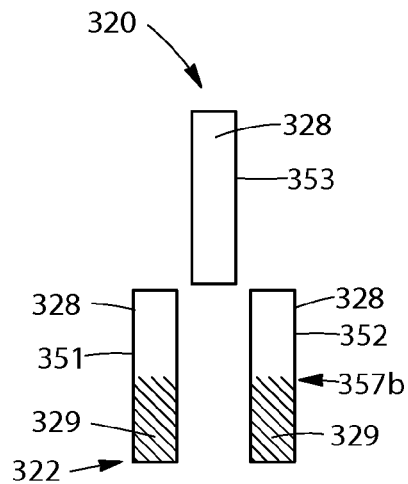
FIG. 3B illustrates a subsequent state of indication for the pattern of visual fullness indicating areas of FIG. 3A, according to embodiments of the present disclosure.

FIG. 3B illustrates a subsequent state of indication for the pattern 320 of FIG. 3A, wherein part of the first visual fullness indicating area 351 and part of the second visual fullness indicating area 353 have changed from an initial visual state 328 to a subsequent visual state 329, to indicate the fullness of the absorbent article 300. In FIG. 3B, a liquid bodily exudate has passed through a portion of the absorbent core of the absorbent article 300 in sufficient concentration to cause a change in visual state from the inboard end 322 of the pattern 320 up through part of the first visual fullness indicating area 351 and up through part of the second visual fullness indicating area 352 to a wet edge 357B.

Throughout the present disclosure, a wet edge refers to a boundary along a visual fullness indicating area of an absorbent article, wherein the boundary indicates an extent of the presence of a liquid bodily exudate. On the inboard side of the wet edge, the visual wetness indicator has experienced the presence of a liquid bodily exudate at a concentration that is sufficient to cause the visual wetness indicator to change visual states. On the outboard side of the wet edge, the visual wetness indicator has not yet experienced the presence of a liquid bodily exudate at a concentration that is sufficient to cause the visual wetness indicator to change visual states.

Figure 3C:
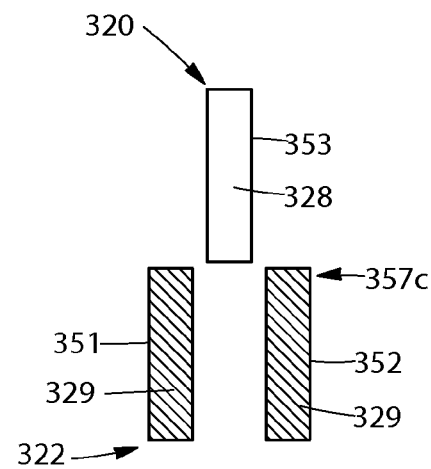
FIG. 3C illustrates a subsequent state of indication for the pattern of visual fullness indicating areas of FIG. 3B, according to embodiments of the present disclosure.

FIG. 3C illustrates a subsequent state of indication for the pattern 320 of FIG. 3B, wherein all of the first visual fullness indicating area 351 and all of the second visual fullness indicating area 352 have changed to the subsequent visual state 329 while all of the third visual fullness indicating area 353 remains in the initial visual state 328, to indicate the fullness of the absorbent article 300. In FIG. 3C, a liquid bodily exudate has passed through a portion of the absorbent core of the absorbent article 300 in sufficient concentration to cause a change in visual state from the inboard end 322 of the pattern 320 up through all of the first visual fullness indicating area 351 and up through all of the second visual fullness indicating area 352 to a wet edge 357C.

Figure 3D:
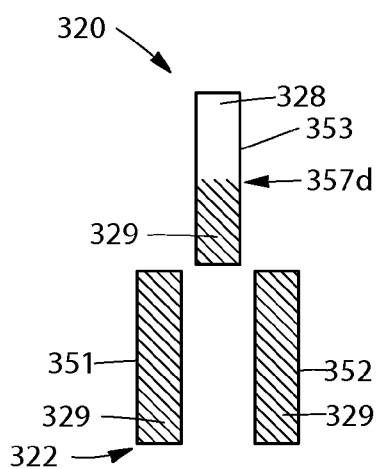
FIG. 3D illustrates a subsequent state of indication for the pattern of visual fullness indicating areas of FIG. 3C, according to embodiments of the present disclosure.

FIG. 3D illustrates a subsequent state of indication for the pattern 320 of FIG. 3C, wherein all of the first visual fullness indicating area 351 and all of the second visual fullness indicating area 352 have changed to the subsequent visual state 329 and part of the third visual fullness indicating area 353 has changed from the initial visual state 328 to the subsequent visual state 329 to indicate the fullness of the absorbent article 300. In FIG. 3D, a liquid bodily exudate has passed through a portion of the absorbent core of the absorbent article 300 in sufficient concentration to cause a change in visual state from the inboard end 322 of the pattern 320 up through all of the first visual fullness indicating area 351, up through all of the second visual fullness indicating area 352, and up through part of the third visual fullness indicating area 353 to a wet edge 357D.

Figure 3E:
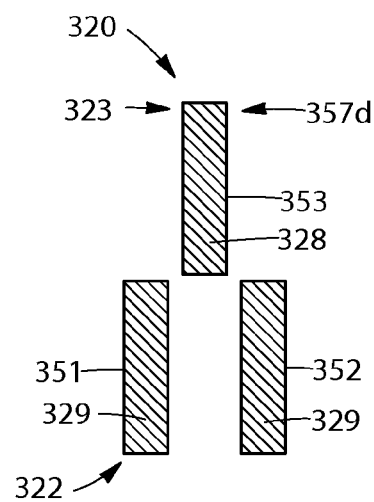
FIG. 3E illustrates a subsequent state of indication for the pattern of visual fullness indicating areas of FIG. 3D, according to embodiments of the present disclosure.

FIG. 3E illustrates a subsequent state of indication for the pattern 320 of FIG. 3D, wherein all of the first visual fullness indicating area 351, all of the second visual fullness indicating area 352, and all of the third visual fullness indicating area 353 have changed to the subsequent visual state 329 to indicate the fullness of the absorbent article 300. In FIG. 3E, a liquid bodily exudate has passed through a portion of the absorbent core of the absorbent article 300 in sufficient concentration to cause a change in visual state from the inboard end 322 of the pattern 320 up through all of the first visual fullness indicating area 351, up through all of the second visual fullness indicating area 352, and up through all of the third visual fullness indicating area 353 to a wet edge 357E, which is near the outboard end 323 of the pattern 320.

Together, FIGS. 3B-3E illustrate that the pattern 320 of visual fullness indicating areas can change visual states progressively and in sequence in the presence of a liquid bodily exudate to indicate the degree to which a liquid bodily exudate has filled the absorbent article 300. In addition to indicating fullness, in embodiments of visual fullness indicating areas throughout the present disclosure, such changes in visual state can also be understood as a signal that indicates the remaining absorbent capacity of an absorbent article and/or as a signal that indicates the risk that an absorbent article may leak.

An appropriate particular location and orientation as well as specific dimensions and other physical characteristics, can be selected for a pattern of visual fullness indicating areas of the present disclosure in order for the visual fullness indicating areas to provide visual state change signals that indicate the degree of fullness, the remaining capacity, and/or the leakage risk for a particular absorbent article. In various embodiments, the absorbent article can include indicia correlating the visual state change signals with fullness, capacity, and/or leakage risk. For each visual fullness indicating area of the present disclosure, the location of the inboard end and the outboard end can be selected to provide visual signals that indicate the degree of fullness, the remaining capacity, and/or the leakage risk for the absorbent article in which the indicating area is included. The degree of fullness, the remaining capacity, and/or the leakage risk for a particular absorbent article can be determined as described in US non-provisional patent application entitled "Absorbent Articles with Primary and Secondary Indicating," filed on Dec. 23, 2009 under Ser. No. 12/646,414, which is incorporated herein by reference.

As a first example, in various embodiments, an inboard end of a first indicating zone can be disposed at a particular location, such that, a change in visual state at that inboard end (i.e. a wet edge proximate to that inboard end) indicates that the absorbent article has: (a) a fullness of about 25%, 30%, 35%, 40%, 45%, 50%, 55%, 60%, 65%, 70%, 75%, 80%, 85%, or any integer of percentage between any of these values, or within any range using any of these values; (b) a remaining capacity of about 75%, 70%, 65%, 60%, 55%, 50%, 45%, 40%, 35%, 30%, 25%, 20%, 15%, or any integer of percentage between any of these values, or within any range using any of these values; and/or (c) a leakage risk of >0%, 5%, 10%, 15%, 20%, 25%, 30%, 35%, 40%, 45%, 50%, 55%, 60%, 65%, 70%, 75%, 80%, 85%, or any integer of percentage between any of these values, or within any range using any of these values. As used herein, the term "leakage risk" refers to the probability of a liquid bodily exudate leaking out of an absorbent article, while the article is being properly worn by a wearer of appropriate size, with such probability being measured in a sufficient number of articles being used by a sufficient number of wearers of appropriate size. For example, at least 100 users should use at least five days worth of articles to determine the probability of an article leaking.

An inboard end of a first indicating zone can be disposed in an absorbent article at any of the following locations: 80 mm, 70 mm, 60 mm, 50 mm, 40 mm, 30 mm, 20 mm, 10 mm, or 5 mm inboard to an outer edge of an acquisition layer; at an outer edge of an acquisition layer; 80 mm, 70 mm, 60 mm, 50 mm, 40 mm, 35 mm, 30 mm, 25 mm, 20 mm, 15 mm, 10 mm, or 5 mm inboard to an outer edge of a distribution layer; at an outer edge of a distribution layer; 140 mm, 130 mm, 120 mm, 110 mm, 100 mm, 90 mm, 80 mm, 70 mm, 60 mm, 50 mm, 40 mm, 30 mm, 20 mm, 10 mm, or 5 mm inboard to an outer edge of an absorbent core; or at an outer edge of an absorbent core. An inboard end of a first indicating zone can also be disposed in an absorbent article at any integer of mm between any of these values or within any range using any of these values.

As a second example, in various embodiments, an outboard end of a first indicating zone can be disposed at a particular location, such that, a change in visual state at that outboard end (i.e. a wet edge proximate to that outboard end) indicates that the absorbent article has: (a) a fullness of 30%, 35%, 40%, 45%, 50%, 55%, 60%, 65%, 70%, 75%, 80%, 85%, 90%, or any integer of percentage between any of these values, or within any range using any of these values; (b) a remaining capacity of 70%, 65%, 60%, 55%, 50%, 45%, 40%, 35%, 30%, 25%, 20%, 15%, 10%, or any integer of percentage between any of these values, or within any range using any of these values; and/or (c) a leakage risk of 30%, 35%, 40%, 45%, 50%, 55%, 60%, 65%, 70%, 75%, 80%, 85%, 90%, or any integer of percentage between any of these values, or within any range using any of these values.

An outboard end of a first indicating zone can be disposed in an absorbent article at any of the following locations: 70 mm, 60 mm, 50 mm, 40 mm, 30 mm, 20 mm, 10 mm, or 5 mm inboard to an outer edge of an acquisition layer; at an outer edge of an acquisition layer; 5 mm or 10 mm outboard from an outer edge of an acquisition layer; 70 mm, 60 mm, 50 mm, 40 mm, 30 mm, 25 mm, 20 mm, 15 mm, 10 mm, or 5 mm inboard to an outer edge of a distribution layer; at an outer edge of a distribution layer; 5 mm or 10 mm outboard from an outer edge of a distribution layer; 130 mm, 120 mm, 110 mm, 100 mm, 90 mm, 80 mm, 70 mm, 60 mm, 50 mm, 40 mm, 30 mm, 20 mm, 10 mm, or 5 mm inboard to an outer edge of an absorbent core; at an outer edge of an absorbent core; or 5 mm or 10 mm outboard from an outer edge of an absorbent core. An outboard end of a first indicating zone can also be disposed in an absorbent article at any integer of mm between any of these values, or within any range using any of these values.

As a third example, in various embodiments, an inboard end of a second indicating zone can be disposed at a particular location, such that, a change in visual state at that inboard end (i.e. a wet edge proximate to that inboard end) indicates that the absorbent article has: (a) a fullness of 50%, 55%, 60%, 65%, 70%, 75%, 80%, 85%, 90%, 95% or any integer of percentage between any of these values, or within any range using any of these values; (b) a remaining capacity of 50%, 45%, 40%, 35%, 30%, 25%, 20%, 15%, 10%, 5%, or any integer of percentage between any of these values, or within any range using any of these values; and/or (c) a leakage risk of 10%, 20%, 30%, 40%, 50%, 60%, 70%, 80%, 90%, or any integer of percentage between any of these values, or within any range using any of these values A change in visual state at an inboard end of a second indicating zone may indicate a fullness that is less than, or equal to, or greater than a fullness indicated by a change in visual state at an outboard end of a first indicating zone. A change in visual state at an inboard end of a second indicating zone may indicate a remaining capacity that is greater than, or equal to, or less than a remaining capacity indicated by a change in visual state at an outboard end of a first indicating zone. A change in visual state at an inboard end of a second indicating zone may indicate a leakage risk that is greater than, or equal to, or less than a leakage risk indicated by a change in visual state at an outboard end of a first indicating zone. A third indicating zone may be related to a second indicating zone in the same way that a second indicating zone relates to a first indicating zone, as described herein. Further, subsequent indicating zones may similarly be related to a prior visual indicating zones.

In various embodiments, a second visual fullness indicating area disposed in the back of an article can have an inboard end disposed with respect to a longitudinally outboard edge of an absorbent core disposed in the front of the article. In this way, the second indicating zone can be configured with respect to a point in the front/center of the article, where liquid bodily exudates are provided to the article by the wearer. As examples, a second indicating zone can be disposed in the back of an article with an inboard end of the indicating area disposed 275 mm, 270 mm, 260 mm, 250 mm, 240 mm, 230 mm, 220 mm, 210 mm, 200 mm, 190 mm, 180 mm, 170 mm, 160 mm, or 150 mm, from a longitudinally outboard edge of an absorbent core disposed in the front of the article. An inboard end of a second indicating zone can also be disposed in an absorbent article at any integer of mm between any of these values, or within any range using any of these values.

As a fourth example, in various embodiments, an outboard end of a second indicating zone can be disposed at a particular location, such that, a change in visual state at that outboard end (i.e. a wet edge proximate to that outboard end) indicates that the absorbent article has: (a) a fullness of 55%, 60%, 65%, 70%, 75%, 80%, 85%, 90%, 95%, about 100%, or any integer of percentage between any of these values, or within any range using any of these values; (b) a remaining capacity of 45%, 40%, 35%, 30%, 25%, 20%, 15%, 10%, 5%, about 0%, or any integer of percentage between any of these values, or within any range using any of these values; and/or (c) a leakage risk of 20%, 30%, 40%, 50%, 60%, 70%, 80%, 90%, about 100%, or any integer of percentage between any of these values, or within any range using any of these values.

An outboard end of a second indicating zone can be disposed in an absorbent article at any of the following locations: 50 mm, 40 mm, 30 mm, 20 mm, 10 mm, or 5 mm inboard to an outer edge of an acquisition layer; at an outer edge of an acquisition layer; 5 mm, 10 mm, 20 mm, or 30 mm outboard from an outer edge of an acquisition layer; 50 mm, 40 mm, 30 mm, 25 mm, 20 mm, 15 mm, 10 mm, or 5 mm inboard to an outer edge of a distribution layer; at an outer edge of a distribution layer; 5 mm, 10 mm, 20 mm, or 30 mm outboard from an outer edge of a distribution layer; 110 mm, 100 mm, 90 mm, 80 mm, 70 mm, 60 mm, 50 mm, 40 mm, 30 mm, 20 mm, or 10 mm inboard to an outer edge of an absorbent core; at an outer edge of an absorbent core; or 5 mm, 10 mm, 20 mm, or 30 mm outboard from an outer edge of an absorbent core. An outboard end of a second indicating zone can also be disposed in an absorbent article at any integer of mm between any of these values, or within any range using any of these values.

It is contemplated that any of the exemplary embodiments described above can be applied in any workable combination to any relevant embodiment of the present disclosure.

Further, in some embodiments, instructions for the absorbent article can explain the correlation between the visual state change signals and fullness, capacity, and/or leakage risk. For example, such instructions can be provided on packaging for the absorbent article or on printed material accompanying the absorbent article. Still further, the correlation between the visual state change signals and fullness, capacity, and/or leakage risk can be communicated through various advertising media.

Further, while embodiments of the present disclosure are drawn toward absorbent articles having patterns of visual fullness indicating areas with overall shapes having relatively wider inboard widths and relatively narrower outboard widths, the present disclosure also contemplates alternate embodiments of absorbent articles having patterns of visual fullness indicating areas configured in an opposite manner, with overall shapes having relatively narrower inboard widths and relatively wider outboard widths. That is, for each disclosed pattern of visual fullness indicating areas, the inboard and outboard directions can also be the reverse of the illustrated embodiment. Each embodiment of the present disclosure can be configured in this opposite manner, as will be understood by one of ordinary skill in the art. These alternate embodiments can also function to indicate different degrees of fullness, capacity, and/or leakage risk as described herein.

Figure 4:
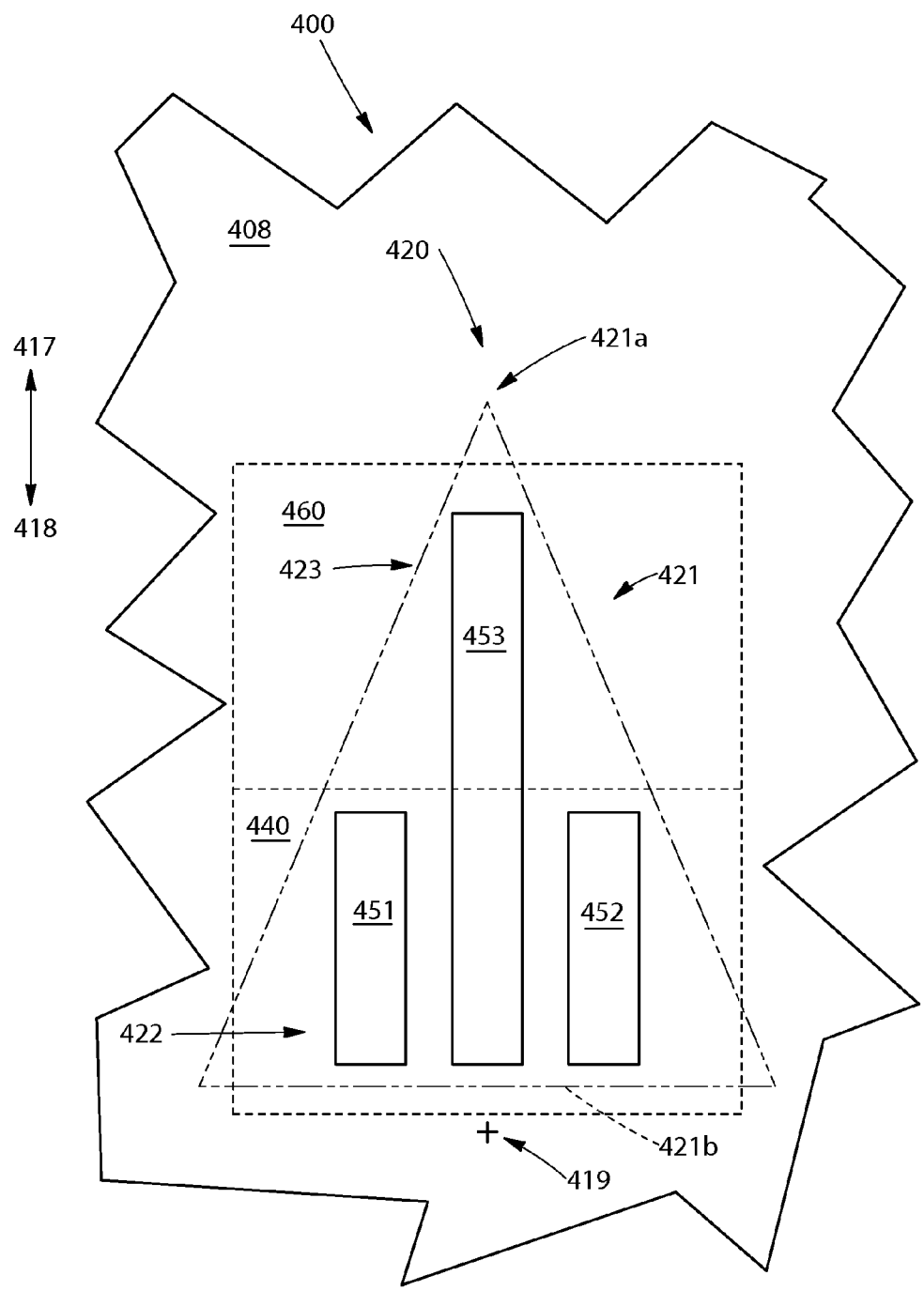
FIG. 4 illustrates a portion of an absorbent article with another pattern of visual fullness indicating areas arranged in two indicating zones wherein the pattern has an overall shape that is triangular, according to embodiments of the present disclosure.

FIG. 4 illustrates an outside plan view of a portion 408 of an absorbent article 400 laid out flat. In various embodiments, the absorbent article 400 can be a disposable wearable absorbent article, such as a pant-type disposable wearable absorbent article or a front-fastenable disposable wearable absorbent article. For reference, FIG. 4 illustrates a center 419 of the absorbent article 400 and arrows indicating relative directions for outboard 417 and inboard 418 for the absorbent article 400. The portion 408 includes a first visual fullness indicating area 451, a second visual fullness indicating area 452, and a third visual fullness indicating area 453, arranged in a pattern 420 with an overall shape 421, including a vertex 421A and a base 421B. The visual fullness indicating areas 451, 452, and 453 are also arranged in a first indicating zone 440 and/or a second indicating zone 460. In various embodiments, the absorbent article 400 can include one or more additional visual fullness indicating areas. Each of the elements of the embodiment of FIG. 4 is configured in the same way as the like-numbered element of the embodiment of FIG. 3A, except as noted below.

Throughout the present disclosure, the term "like-numbered" is intended to indicate a correspondence between labels of elements wherein the last two numbers in the labels of the elements are the same. Element labels are considered to be like-numbered despite differing numeral prefixes corresponding to figure numbers, and despite differing alphabetical suffixes corresponding to particular embodiments.

In the embodiment of FIG. 4, the third visual fullness indicating area 453 is longer than the first visual fullness indicating area 451 and the second visual fullness indicating area 452.

The first indicating zone 440 includes all of the first visual fullness indicating area 451 and all of the second visual fullness indicating area 452, as well as a portion of the third visual fullness indicating area 453. Thus, the first indicating zone 440 includes at least a portion of three visual fullness indicating areas; the first number is three. The second indicating zone 460 includes a portion of the third visual fullness indicating area 453. Thus, the second indicating zone 460 includes at least a portion of one visual fullness indicating area; the second number is one. In the embodiment of FIG. 4, the first number (three) is greater than the second number (one).

The pattern 420 can be configured such that the visual fullness indicating areas 451, 452, and 453 change visual states progressively and in sequence, similar to the embodiment illustrated with FIGS. 3B-3E, with some differences, as described below. First, the first visual fullness indicating area 451, the second visual fullness indicating area 452, and the portion of the third visual fullness indicating area 453 included in the first indicating zone 460 can change from an initial visual state to a subsequent visual state when indicating the presence of a liquid bodily exudate in the absorbent article 400. Second, the portion of the third visual fullness indicating area 453 included in the second indicating zone 460 can change from an initial visual state to a subsequent visual state when indicating the presence of a liquid bodily exudate in the absorbent article 300. The partial or complete absence or presence of the subsequent visual state(s) in the visual fullness indicating areas 451, 452, and 453 of the pattern 420 can indicate the fullness of the absorbent article 400.

Since the visual fullness indicating areas 451, 452, and 453 are arranged in the pattern 420 with a distinct triangular overall shape 421, the indicating areas are easy to understand. Also, since at least a portion of three visual fullness indicating areas are arranged in the first indicating zone 440 and at least a portion of one visual fullness indicating area is arranged in the second indicating zone 460, the indicating areas are easy to understand. The pattern and the zones can help provide certainty about the fullness of the absorbent article 400. By knowing the fullness of the absorbent article 400, the absorbent article 400 can be changed after a wearer has appropriately utilized its capacity and/or before it is likely to leak.

In one alternate embodiment, the portion 408 of the absorbent article 400 can be configured as described above in connection with the embodiment of FIG. 4, except that the second visual fullness indicating area 452 may be omitted from the pattern 420. In this alternate embodiment, the first indicating zone 440 would include at least a portion of two visual fullness indicating areas, so the first number would be two, which would still be greater than the second number (one). Also in this alternate embodiment, an overall shape 421 of the pattern 420 would be a right triangle.

In another alternate embodiment, the portion 408 of the absorbent article 400 can be configured as described above in connection with the embodiment of FIG. 4, except that the third visual fullness indicating area 453 may be divided into two separate visual fullness indicating areas; one in the first indicating zone 440 and one in the second indicating zone 460. In this alternate embodiment, the first number would still be three, and the second number would still be one.

Figure 5:
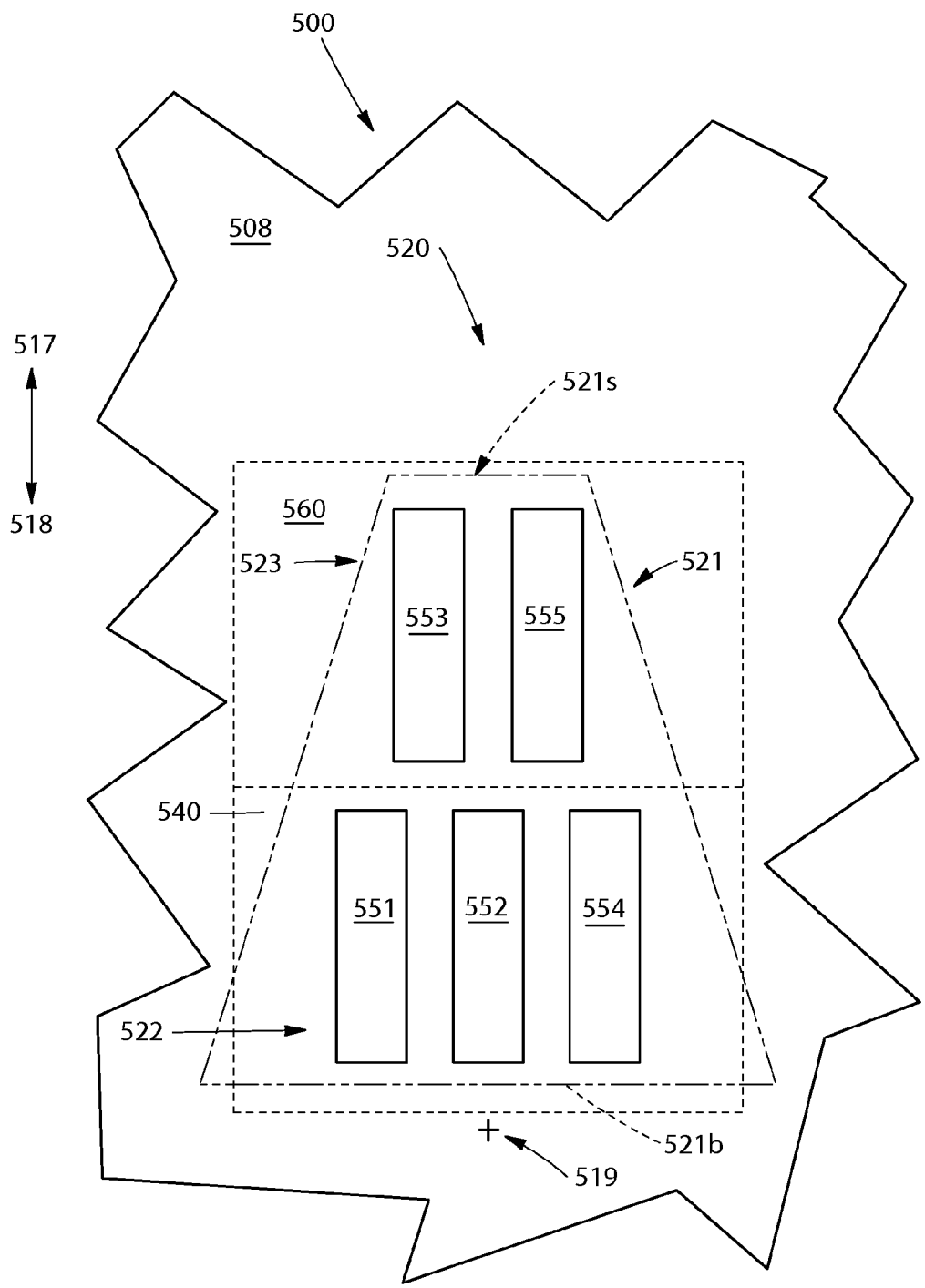
FIG. 5 illustrates a portion of an absorbent article with a pattern of visual fullness indicating areas arranged in two indicating zones wherein the pattern has an overall shape that is trapezoidal, according to embodiments of the present disclosure.

FIG. 5 illustrates an outside plan view of a portion 508 of an absorbent article 500 laid out flat. In various embodiments, the absorbent article 500 can be a disposable wearable absorbent article, such as a pant-type disposable wearable absorbent article or a front-fastenable disposable wearable absorbent article. For reference, FIG. 5 illustrates a center 519 of the absorbent article 500 and arrows indicating relative directions for outboard 517 and inboard 518 for the absorbent article 500. The portion 508 includes a first visual fullness indicating area 551, a second visual fullness indicating area 552, a third visual fullness indicating area 553, a fourth visual fullness indicating area 554, and a fifth visual fullness indicating area 555, arranged in a pattern 520 with an overall shape 521, including a base 521B disposed proximate to an inboard end 522 of the pattern 520 and an opposite side 521S disposed proximate to an outboard end 523 of the pattern 520. The visual fullness indicating areas 551, 552, 553, 554, and 555 are also arranged in a first indicating zone 540 and/or a second indicating zone 560. In various embodiments, the absorbent article 500 can include one or more additional visual fullness indicating areas. Each of the elements of the embodiment of FIG. 5 is configured in the same way as the like-numbered element of the embodiment of FIG. 3A, except as noted below.

The fourth visual fullness indicating area 554 and the fifth visual fullness indicating area 555 are each configured in the same way as the first visual fullness indicating area 551, the second visual fullness indicating area 552, and the third visual fullness indicating area 553. The fourth visual fullness indicating area 554 and the fifth visual fullness indicating area 555 are disposed within the portion 508 as described below.

The visual fullness indicating areas 551, 552, 553, 554, and 555 are arranged in the pattern 520 such that the pattern 520 is recognizable as having a distinctive overall shape 521. In the embodiment of FIG. 5, the overall shape 521 of the pattern 520 is trapezoidal. However, in various embodiments, an overall shape of a pattern may only be substantially trapezoidal. The trapezoidal overall shape 521 includes a base 521B disposed proximate to the inboard end 522 as well as an opposite side 521S disposed opposite from and parallel to the base 521B. The trapezoidal overall shape 521 is an isosceles trapezoid. However, in various embodiments, a trapezoidal overall shape can be any kind of quadrilateral with at least one pair of parallel lines for sides.

In the embodiment of FIG. 5, the first indicating zone 540 includes all of the first visual fullness indicating area 551, all of the second visual fullness indicating area 552, and all of the fourth visual fullness indicating area 554. Thus, the first indicating zone 540 includes at least a portion of three visual fullness indicating areas; the first number is three. The second indicating zone 560 includes all of the third visual fullness indicating area 553 and all of the fourth visual fullness indicating area 554. Thus, the second indicating zone 560 includes at least a portion of two visual fullness indicating areas; the second number is two. In the embodiment of FIG. 5, the first number (three) is greater than the second number (two).

Since the visual fullness indicating areas 551, 552, and 553 are arranged in the pattern 520 with a distinct trapezoidal overall shape 521, the indicating areas are easy to understand. Also, since three visual fullness indicating areas are arranged in the first indicating zone 540 and two visual fullness indicating areas are arranged in the second indicating zone 560, the indicating areas are easy to understand. The pattern and the zones can help provide certainty about the fullness of the absorbent article 500. By knowing the fullness of the absorbent article 500, the absorbent article 500 can be changed after a wearer has appropriately utilized its capacity and/or before it is likely to leak.

In alternate embodiments, the portion 508 of the absorbent article 500 can be configured as described above in connection with the embodiment of FIG. 5, except that a visual fullness indicating area of the first zone may be joined with a visual fullness indicating area of the second zone. For example, the first visual fullness indicating area 551 may be joined with the second visual fullness indicating area 553 to form a single visual fullness indicating area with a portion in the first indicating zone 540 and a portion in the second indicating zone 560. In this alternate embodiment, the first number would still be three, and the second number would still be two.

Figure 6:
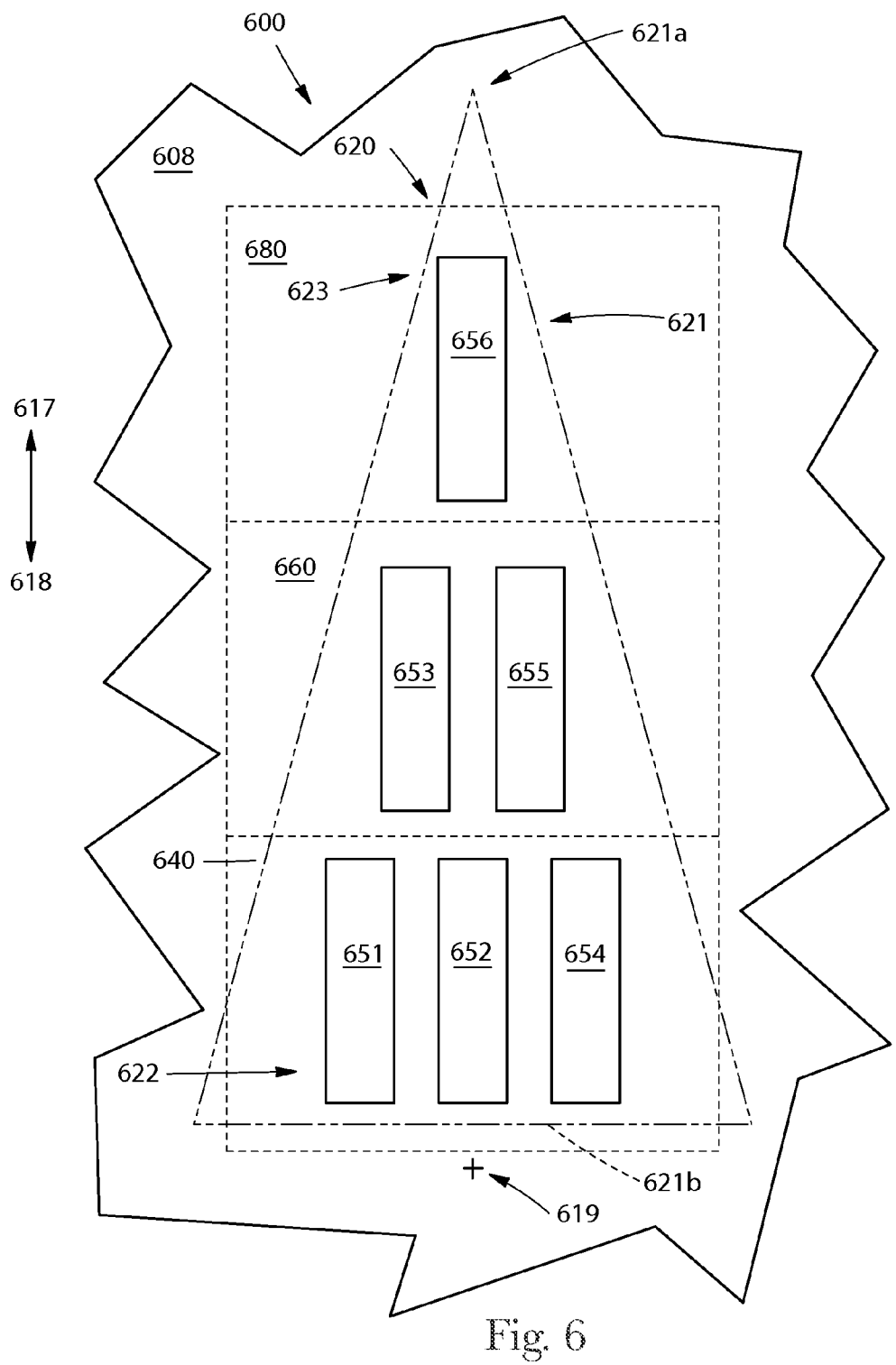
FIG. 6 illustrates a portion of an absorbent article with a pattern of visual fullness indicating areas arranged in three indicating zones wherein the pattern has an overall shape that is triangular, according to embodiments of the present disclosure.

FIG. 6 illustrates an outside plan view of a portion 608 of an absorbent article 600 laid out flat. In various embodiments, the absorbent article 600 can be a disposable wearable absorbent article, such as a pant-type disposable wearable absorbent article or a front-fastenable disposable wearable absorbent article. For reference, FIG. 6 illustrates a center 619 of the absorbent article 600 and arrows indicating relative directions for outboard 617 and inboard 618 for the absorbent article 600. The portion 608 includes a first visual fullness indicating area 651, a second visual fullness indicating area 652, a third visual fullness indicating area 653, a fourth visual fullness indicating area 654, a fifth visual fullness indicating area 655, and a sixth visual fullness indicating area 656, arranged in a pattern 620 with an overall shape 621, including a base 621B disposed proximate to an inboard end 622 of the pattern as well as a vertex 621A disposed proximate to an outboard end 623 of the pattern. The visual fullness indicating areas 651, 652, 653, 654, 655, and 656 are also arranged in a first indicating zone 640, and/or a second indicating zone 660, and/or a third indicating zone 680. In various embodiments, the absorbent article 600 can include one or more additional visual fullness indicating areas. Each of the elements of the embodiment of FIG. 6 is configured in the same way as the like-numbered element of the embodiment of FIG. 5, except as noted below.

The sixth visual fullness indicating area 656 is configured in the same way as the first visual fullness indicating area 651, the second visual fullness indicating area 652, the third visual fullness indicating area 653, the fourth visual fullness indicating area 654, and the fifth visual fullness indicating area 655. The sixth visual fullness indicating area 656 is disposed within the portion 608 as described below.

The visual fullness indicating areas 651, 652, 653, 654, 655, and 656 are arranged in the pattern 620 such that the pattern 620 is recognizable as having a distinctive overall shape 621. In the embodiment of FIG. 6, the overall shape 621 of the pattern 620 is triangular. The triangular overall shape 621 includes the base 621B disposed proximate to the inboard end 622 as well as the vertex 621A disposed proximate to the outboard end 623. The triangular overall shape 621 is an isosceles triangle.

In the embodiment of FIG. 6, the first indicating zone 640 includes all of the first visual fullness indicating area 651, all of the second visual fullness indicating area 652, and all of the fourth visual fullness indicating area 654. Thus, the first indicating zone 640 includes at least a portion of three visual fullness indicating areas; the first number is three. The second indicating zone 660 includes all of the third visual fullness indicating area 653 and all of the fourth visual fullness indicating area 654. Thus, the second indicating zone 660 includes at least a portion of two visual fullness indicating areas; the second number is two. In the embodiment of FIG. 6, the first number (three) is greater than the second number (two).

In embodiments having a first indicating zone, a second indicating zone, and a third indicating zone the third indicating zone has an overall width that is equal to an overall width of a second indicating zone. A third indicating zone has an overall length that can be less than, equal to, or greater than a second indicating zone. A third indicating zone is immediately adjacent to a second indicating zone. Substantially all or all of a third indicating zone is outboard from a second indicating zone.

The third indicating zone 680 includes all of the sixth visual fullness indicating area 656. Thus, the third indicating zone 680 includes at least a portion of one visual fullness indicating area; the third number is one. In the embodiment of FIG. 6, the second number (two) is greater than the third number (three).

Since the visual fullness indicating areas 651, 652, 653, 654, 655, and 656 are arranged in the pattern 620 with a distinct triangular overall shape 621, the indicating areas are easy to understand. Also, since three visual fullness indicating areas are arranged in the first indicating zone 640, two visual fullness indicating areas are arranged in the second indicating zone 660, and three visual fullness indicating areas are arranged in the third indicating zone 680 the indicating areas are easy to understand. The pattern and the zones can help provide certainty about the fullness of the absorbent article 600. By knowing the fullness of the absorbent article 600, the absorbent article 600 can be changed after a wearer has appropriately utilized its capacity and/or before it is likely to leak.

In alternate embodiments, the portion 608 of the absorbent article 600 can be configured as described above in connection with the embodiment of FIG. 6, except that a visual fullness indicating area of the second zone may be joined with the visual fullness indicating area of the third zone. For example, the third visual fullness indicating area 653 may be joined with the sixth visual fullness indicating area 656 to form a single visual fullness indicating area with a portion in the second indicating zone 560 and a portion in the third indicating zone 580. In this alternate embodiment, the first number would still be three, the second number would still be two, and the third number would still be one.

Figure 7:
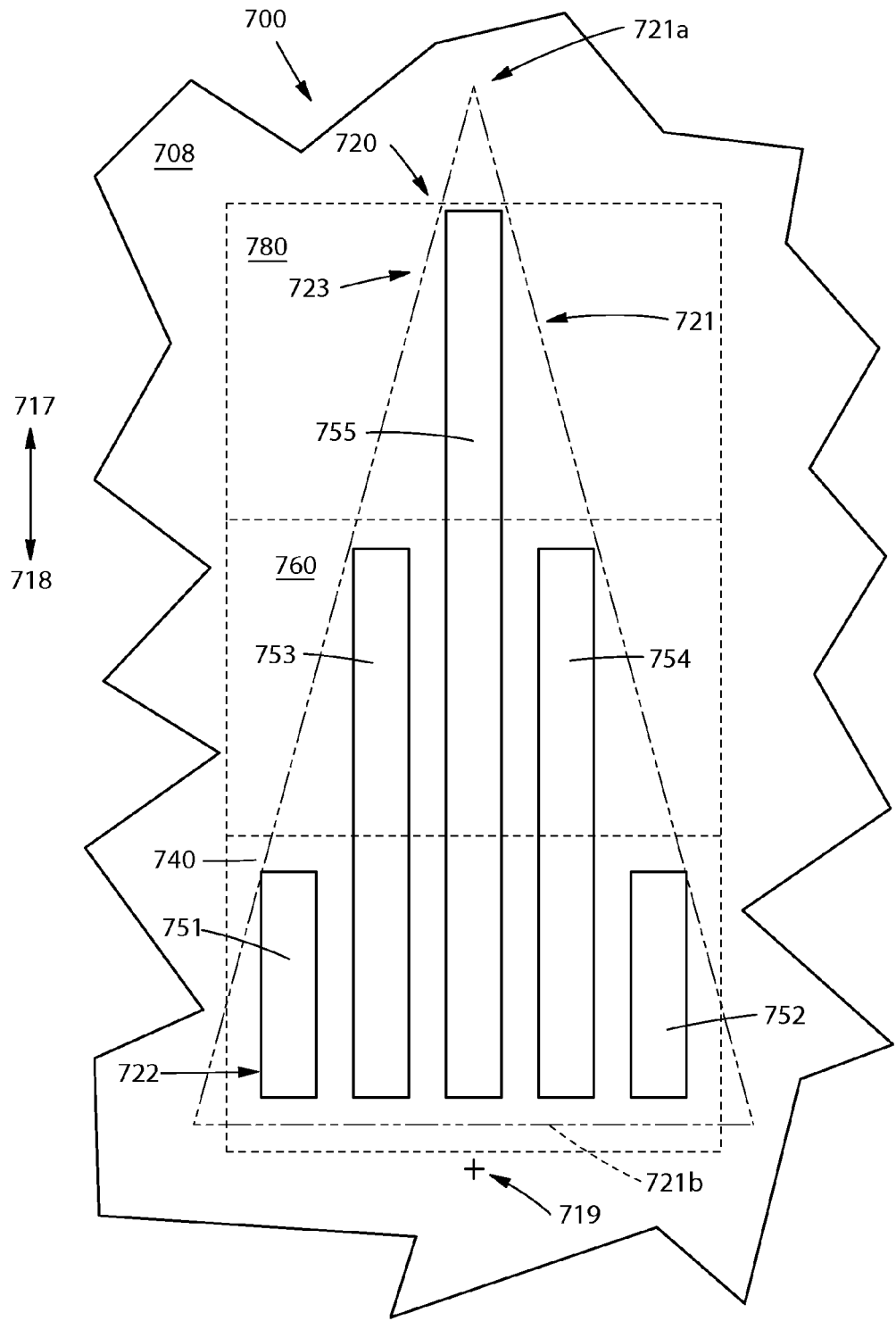
FIG. 7 illustrates a portion of an absorbent article with another pattern of visual fullness indicating areas arranged in three indicating zones wherein the pattern has an overall shape that is triangular, according to embodiments of the present disclosure.

FIG. 7 illustrates an outside plan view of a portion 708 of an absorbent article 700 laid out flat. In various embodiments, the absorbent article 700 can be a disposable wearable absorbent article, such as a pant-type disposable wearable absorbent article or a front-fastenable disposable wearable absorbent article. For reference, FIG. 7 illustrates a center 719 of the absorbent article 700 and arrows indicating relative directions for outboard 717 and inboard 718 for the absorbent article 700. The portion 708 includes a first visual fullness indicating area 751, a second visual fullness indicating area 752, a third visual fullness indicating area 753, a fourth visual fullness indicating area 754, a fifth visual fullness indicating area 755, and a sixth visual fullness indicating area 756, arranged in a pattern 720 with an overall shape 721, including a base 721B disposed proximate to an inboard end 722 of the pattern as well as a vertex 721A disposed proximate to an outboard end 723 of the pattern. The visual fullness indicating areas 751, 752, 753, 754, 755, and 756 are also arranged in a first indicating zone 740, and/or a second indicating zone 760, and/or a third indicating zone 780. In various embodiments, the absorbent article 700 can include one or more additional visual fullness indicating areas. Each of the elements of the embodiment of FIG. 7 is configured in the same way as the like-numbered element of the embodiment of FIG. 4, except as noted below.

The fourth visual fullness indicating area 754 is configured in the same way as the third visual fullness indicating area 753. The fifth visual fullness indicating area 755 is configured in the same way as the third visual fullness indicating area 753, except that the fifth visual fullness indicating area 755 is longer and extends into the third indicating zone 780.

The visual fullness indicating areas 751, 752, 753, 754, 755, and 756 are arranged in the pattern 720 such that the pattern 720 is recognizable as having a distinctive overall shape 721. In the embodiment of FIG. 7, the overall shape 721 of the pattern 720 is triangular. The triangular overall shape 721 includes the base 721B disposed proximate to the inboard end 722 as well as the vertex 721A disposed proximate to the outboard end 723. The triangular overall shape 721 is an isosceles triangle.

In the embodiment of FIG. 7, the first indicating zone 740 includes all of the first visual fullness indicating area 751 and all of the second visual fullness indicating area 752, as well as a portion of the third visual fullness indicating area 753, a portion of the fourth visual fullness indicating area 754, and a portion of the fifth visual fullness indicating area 755. Thus, the first indicating zone 740 includes at least a portion of five visual fullness indicating areas; the first number is five. The second indicating zone 760 includes a portion of the third visual fullness indicating area 753, a portion of the fourth visual fullness indicating area 754, and a portion of the fifth visual fullness indicating area 755. Thus, the second indicating zone 760 includes at least a portion of three visual fullness indicating areas; the second number is three. The third indicating zone 780 includes a portion of the fifth visual fullness indicating area 755. Thus, the third indicating zone 780 includes at least a portion of one visual fullness indicating area; the third number is one. In the embodiment of FIG. 7, the first number (five) is greater than the second number (three), which is greater than the third number (one).

Since the visual fullness indicating areas 751, 752, 753, 754, and 755 are arranged in the pattern 720 with a distinct triangular overall shape 721, the indicating areas are easy to understand. Also, since at least a portion of five visual fullness indicating areas are arranged in the first indicating zone 740, at least a portion of three visual fullness indicating areas are arranged in the second indicating zone 760, and at least a portion of one visual fullness indicating area is arranged in the third indicating zone 780 the indicating areas are easy to understand. The pattern and the zones can help provide certainty about the fullness of the absorbent article 700. By knowing the fullness of the absorbent article 700, the absorbent article 700 can be changed after a wearer has appropriately utilized its capacity and/or before it is likely to leak.

In one alternate embodiment, the portion 708 of the absorbent article 700 can be configured as described above in connection with the embodiment of FIG. 7, except that the second visual fullness indicating area 752 and the fourth visual fullness indicating area 754 may be omitted. In this alternate embodiment, the first indicating zone 740 would include at least a portion of three visual fullness indicating areas and the second indicating zone 760 would include at least a portion of two visual fullness indicating areas; so the first number would be three, which would still be greater than the second number (two), which would still be greater than the third number (one). Also in this alternate embodiment, an overall shape of the pattern 720 would be a right triangle.

In another alternate embodiment, the portion 708 of the absorbent article 700 can be configured as described above in connection with the embodiment of FIG. 7, except that the fifth visual fullness indicating area 755 may be shortened to no longer extend into the third indicating zone 780. In this alternate embodiment, the first indicating zone 740 would still include at least a portion of five visual fullness indicating areas and the second indicating zone 760 would still include at least a portion of four visual fullness indicating areas, but there would be no third indicating zone. Also in this alternate embodiment, an overall shape of the pattern 720 would be a trapezoid.

The present disclosure includes absorbent articles with wetness indicating areas that are easy to understand. As a result, these wetness indicating areas can help provide certainty about the fullness of absorbent articles. By knowing how full an article is, the article can be changed after the wearer has appropriately utilized the capacity of the article. Also, by knowing how full an article is, the article can be changed before it is likely to leak.

Further, the present disclosure contemplates that an absorbent article, such as a disposable wearable absorbent article, can have one or more visual fullness indicators configured as described herein and further configured with various additional and/or alternate structures and/or functions as described below.

One or more embodiments of the present disclosure can be combined with one or more embodiments of U.S. non-provisional patent application Ser. No. 12/346,445 entitled "Disposable Wearable Absorbent Articles with Multiple Indicating Colors," filed on Dec. 30, 2008 under attorney docket number 11217Q and/or US non-provisional patent application entitled "Disposable Wearable Absorbent Articles with Multiple Indicating Colors," filed on Dec. 23, 2009 and further identified by Ser. No. 12/646,296, each of which is incorporated herein by reference. A disposable wearable absorbent article with patterns of indicating can also have multiple indicating colors.

One or more embodiments of the present disclosure can be combined with one or more embodiments of U.S. non-provisional patent application Ser. No. 12/346,481 entitled "Absorbent Articles with Multiple Indicating Widths," filed on Dec. 30, 2008 under attorney docket number 11218Q and/or US non-provisional patent application entitled "Absorbent Articles with Multiple Indicating Widths," filed on Dec. 23, 2009 under Ser. No. 12/646,315, each of which is incorporated herein by reference. A disposable wearable absorbent article with patterns of indicating can also have multiple indicating widths.

One or more embodiments of the present disclosure can be combined with one or more embodiments of U.S. non-provisional patent application Ser. No. 12/346,496 entitled "Disposable Wearable Absorbent Articles with Gender Specific Indicia," filed on Dec. 30, 2008 under attorney docket number 11219 and/or US non-provisional patent application entitled "Disposable Wearable Absorbent Articles with Gender Specific Indicia," filed on Dec. 23, 2009 under Ser. No. 12/646,334, each of which is incorporated herein by reference. A disposable wearable absorbent article with patterns of indicating can also have gender specific indicia.

One or more embodiments of the present disclosure can be combined with one or more embodiments of U.S. non-provisional patent application Ser. No. 12/346,510 entitled "Disposable Wearable Absorbent Articles with Gender Specific Indicating," filed on Dec. 30, 2008 under attorney docket number 11220 and/or US non-provisional patent application entitled "Disposable Wearable Absorbent Articles with Gender Specific Indicating," filed on Dec. 23, 2009 and further identified by Ser. No. 12/646,354, each of which is incorporated herein by reference. A disposable wearable absorbent article with patterns of indicating can also have gender specific indicia.

One or more embodiments of the present disclosure can be combined with one or more embodiments of U.S. provisional patent application 61/141,573 entitled "Absorbent Articles with Primary and Secondary Indicating," filed on Dec. 30, 2008 under attorney docket number 11222PQ and/or US non-provisional patent application entitled "Absorbent Articles with Primary and Secondary Indicating," filed on Dec. 23, 2009 under 12/646,414, each of which is incorporated herein by reference. A disposable wearable absorbent article with patterns of indicating can also have primary and secondary indicating.

One or more embodiments of the present disclosure can be combined with one or more embodiments of US non-provisional patent application entitled "Absorbent Articles with Primary and Secondary Indicia," filed on Dec. 23, 2009 under 12/646,430, which is incorporated herein by reference. A disposable wearable absorbent article with patterns of indicating can also have primary and secondary indicia.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article, comprising:
   a longitudinal centerline and a lateral centerline;
   a number of visual fullness indicating areas arranged in a distinct pattern with an overall shape that is selected from the group consisting of triangular and trapezoidal;
   a first indicating zone having a first number of visual fullness indicating area(s) spaced laterally from each other, each having a portion of which lies within the area of the first indicating zone;
   a second indicating zone having a second number of visual fullness indicating area(s) spaced laterally from each other, each having a portion of which lies within the area of the second indicating zone;
   wherein the second indicating zone is immediately adjacent to and longitudinally outboard from the first indicating zone;
   the second number of visual fullness indicating areas differs from the first number of visual fullness indicating areas; and
   the first indicating zone does not include a portion of any of the second number of visual fullness indicating area(s) of the second indicating zone.

2. The absorbent article of claim 1 wherein all of the visual fullness indicating areas have substantially the same size and shape.

3. The absorbent article of claim 1, which is a disposable absorbent article.

4. The disposable absorbent article of claim 3, which is a disposable wearable absorbent article.

5. The absorbent article of claim 1, wherein each of the number of visual fullness indicating areas has an overall shape that is substantially elongated.

6. The absorbent article of 1, including one or more other wetness indicators besides the number of visual fullness indicating areas, wherein at an outboard end of the pattern each of the number of visual fullness indicating areas is spaced apart from each of the other wetness indicators by a spaced apart distance of at least 20 millimeters.

7. The absorbent article of claim 6, wherein each of the number of visual fullness indicating areas is spaced apart from each of the other wetness indicators by a spaced apart distance of at least 20 millimeters.

8. The absorbent article of claim 1, wherein the overall shape is triangular and includes a base proximate to an inboard end of the pattern as well as a vertex proximate to an outboard end of the pattern.

9. The absorbent article of claim 1, wherein the overall shape is trapezoidal and includes a base with a wider width proximate to an inboard end of the pattern as well as an opposite side with a narrower width opposite from the base and proximate to an outboard end of the pattern.

10. The absorbent article of claim 1, including a third indicating zone with at least a portion of each of a third number of visual fullness indicating areas, wherein the third indicating zone is immediately adjacent to the second indicating zone, the third indicating zone is outboard from the second indicating zone, an overall width of the third indicating zone is equal to an overall width of the second indicating zone, and the third number differs from the second number.

11. The absorbent article of claim 10, wherein the third number is less than the second number.

* * * * *